(12) United States Patent
Kim et al.

(10) Patent No.: US 12,151,014 B2
(45) Date of Patent: Nov. 26, 2024

(54) GLOSS LIP BALM FORMULATION

(71) Applicant: MAST INDUSTRIES (FAR EAST) LIMITED, Kowloon (HK)

(72) Inventors: Phil Kim, North Brunswick, NJ (US); Lisa Nichols, Kew Gardens, NY (US); Marta Palladino, New York, NY (US)

(73) Assignee: MAST INDUSTRIES (FAR EAST) LIMITED, Hong Kong (CN)

( * ) Notice: Subject to any disclaimer, the term of this patent is extended or adjusted under 35 U.S.C. 154(b) by 0 days.

(21) Appl. No.: 15/707,053

(22) Filed: Sep. 18, 2017

(65) Prior Publication Data

US 2019/0083379 A1    Mar. 21, 2019

(51) Int. Cl.
| | | |
|---|---|---|
| *A61K 8/891* | (2006.01) | |
| *A61K 8/02* | (2006.01) | |
| *A61K 8/37* | (2006.01) | |
| *A61K 8/39* | (2006.01) | |
| *A61K 8/92* | (2006.01) | |
| *A61Q 1/04* | (2006.01) | |

(52) U.S. Cl.
CPC ............ *A61K 8/891* (2013.01); *A61K 8/0229* (2013.01); *A61K 8/37* (2013.01); *A61K 8/39* (2013.01); *A61K 8/925* (2013.01); *A61K 8/927* (2013.01); *A61Q 1/04* (2013.01)

(58) Field of Classification Search
CPC ............ A61K 8/891; A61K 8/39; A61K 8/585
See application file for complete search history.

(56) References Cited

U.S. PATENT DOCUMENTS

| | | | |
|---|---|---|---|
| 5,302,377 A | | 4/1994 | Pereira et al. |
| 5,455,025 A | | 10/1995 | Pereira et al. |
| 5,556,613 A | | 9/1996 | Arnaud et al. |
| 5,558,071 A | * | 9/1996 | Ward ................. F02P 3/02 123/598 |
| 5,597,555 A | | 1/1997 | Pereira et al. |
| 5,693,316 A | | 12/1997 | Pereira et al. |
| 5,932,197 A | | 8/1999 | Arnaud |
| 6,136,332 A | | 10/2000 | Grollier et al. |
| 6,579,851 B2 | * | 6/2003 | Goeke ................. A61K 38/26 514/11.7 |
| 7,217,424 B2 | | 5/2007 | Pereira et al. |
| 7,253,302 B2 | | 8/2007 | Smith et al. |
| 7,820,146 B2 | | 10/2010 | Ferrari et al. |
| 8,461,129 B2 | * | 6/2013 | Bolduc ................. A61L 15/28 127/49 |
| 2006/0165640 A1 | * | 7/2006 | Lebre ................. A61Q 1/06 424/70.22 |
| 2007/0258925 A1 | | 11/2007 | Bui et al. |
| 2011/0028412 A1 | * | 2/2011 | Cappello ............ A61K 31/7004 514/25 |
| 2013/0041004 A1 | * | 2/2013 | Drager ................. A61K 9/08 514/394 |
| 2013/0084243 A1 | * | 4/2013 | Goetsch ............. C07K 16/2863 424/1.49 |
| 2013/0096073 A1 | * | 4/2013 | Sidelman ........... A61K 38/1709 514/21.6 |
| 2014/0093462 A1 | | 4/2014 | Osawa et al. |
| 2016/0303004 A1 | * | 10/2016 | Ma ........................ A61K 8/602 |

FOREIGN PATENT DOCUMENTS

| | | |
|---|---|---|
| WO | WO 2013/190703 | 12/2013 |
| WO | WO 2013/191300 A1 | 12/2013 |
| WO | WO-2016/027092 A1 | 2/2016 |

OTHER PUBLICATIONS

Gao, T. et al. "A new multifunctional, shine-enhancing emollient: PPG-3 benzyl ether myristate" J. Cosmet. Sci., 55 (Supplement), S143-S150 (2004) (Year: 2004).*
Canadian Search Report was dated Sep. 9, 2020 by the Canadian Patent Office for CA Application No. 3,017,384, filed on Sep. 13, 2018 (Applicant-Limited Brands, Inc.) (4 Pages).
"MILK Makeup Lip Vinyl", anonymity, http://www.cosdna.com/cht/cosmetic 55f6297552.html, pp. 1-2.

* cited by examiner

*Primary Examiner* — Andrew S Rosenthal
(74) *Attorney, Agent, or Firm* — Ballard Spahr LLP

(57) ABSTRACT

The disclosure relates to pre-blend compositions and methods of making the compositions. The disclosure also relates to cosmetic compositions prepared from the pre-blend compositions and methods of making same. This abstract is intended as a scanning tool for purposes of searching in the particular art and is not intended to be limiting of the present invention.

29 Claims, No Drawings

GLOSS LIP BALM FORMULATION

FIELD OF THE INVENTION

The present invention relates to pre-blend compositions and methods of making the compositions. The invention also relates to cosmetic compositions prepared from the pre-blend compositions and methods of making same.

BACKGROUND

Cosmetic products designed for use on the lips typically fall into two categories: those that are used to alter the visual appearance of the lips and those that are used to benefit the health of the lips. Lip gloss, which primarily exists in "liquid" form, generally falls into the former category, being used primarily to provide shine and color. Unfortunately, these glosses tend to be tacky, stringy, and, if they have lower viscosity oils with slip, may exhibit bleeding, migration, and leeching of colorants. Hot pour lipsticks that are advertised with shine have been unsuccessful at offering a comparable shine performance. These same drawbacks, however, are often not present in lip balms. Lip balms fall into the latter category, being used to provide moisture or other skincare related benefits. They do not advertise gloss or shine.

Despite a wide selection of cosmetic products that offer high performance shine or hydration, a multifunctional composition that amply provides both advantages has yet to be realized. Thus, there remains a need for cosmetic compositions that provide a superior shine without tackiness or bleeding while also hydrating and moisturizing. These needs and others are met by the present invention.

SUMMARY

In accordance with the purpose(s) of the invention, as embodied and broadly described herein, the invention, in one aspect, relates to oxygen scavenging compositions, methods of making the compositions, articles prepared from the compositions, and methods of making the articles.

Disclosed are pre-blend compositions comprising: (a) a methyl phenyl silicone ester in an amount of from about 20 wt % to about 60 wt %; (b) an aromatic ester having a structure represented by a formula:

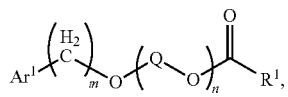

wherein m is an integer selected from 0 and 1; wherein n is an integer from 1 to 20; wherein each Q is independently C1-C6 acyclic alkyl; wherein $R^1$ is a C4-C24 acyclic alkyl; wherein $Ar^1$ is aryl substituted with 0, 1, 2, or 3 groups independently selected from halogen, C1-C4 alkyl, C1-C4 alkylene, C1-C4 alkoxy, —(C1-C8 alkyl)$Ar^2$, —$SO_2Ar^2$, and $Ar^2$; and wherein $Ar^2$ is selected from monocyclic aryl and bicyclic aryl and substituted with 0, 1, 2, or 3 groups independently selected from halogen, C1-C4 alkyl, C1-C4 alkylene, and C1-C4 alkoxy, in an amount of from about 20 wt % to about 60 wt %; and (c) a mixed ester composition in an amount of from about 10 wt % to about 30 wt %, wherein the mixed ester composition comprises a blend of: (i) a mixed ester having a structure represented by a formula:

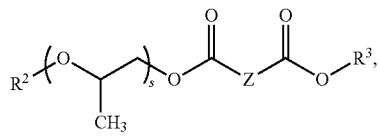

wherein s is an integer from 3 to 10; wherein Z is C4-C40 acyclic alkyl substituted with 0, 1, 2, or 3 independently selected C1-C10 alkylene groups; wherein $R^2$ is C4-C24 acyclic alkyl; and wherein $R^3$ is C4-C24 acyclic alkyl; and a wax component.

Also disclosed are cosmetic compositions comprising: (a) a cosmetic base component comprising a disclosed pre-blend composition; (b) a first pigment; (c) an emollient; and (d) a long chain fatty alcohol.

Also disclosed are method of makings a cosmetic composition, the method comprising the step of combining: (a) a cosmetic base comprising a disclosed pre-blend composition; (b) a first pigment; (c) an emollient; and (d) a long chain fatty alcohol, thereby making the cosmetic composition.

Also disclosed are methods of making a pre-blend composition, the method comprising the step of combining: (a) a methyl phenyl silicone ester in an amount of from about 20 wt % to about 60 wt %; (b) an aromatic ester having a structure represented by a formula:

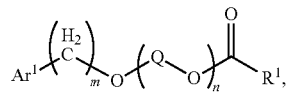

wherein m is an integer selected from 0 and 1; wherein n is an integer from 1 to 20; wherein each Q is independently C1-C6 acyclic alkyl; wherein $R^1$ is a C4-C24 acyclic alkyl; wherein $Ar^1$ is aryl substituted with 0, 1, 2, or 3 groups independently selected from halogen, C1-C4 alkyl, C1-C4 alkylene, C1-C4 alkoxy, —(C1-C8 alkyl)$Ar^2$, —$SO_2Ar^2$, and $Ar^2$; and wherein $Ar^2$ is selected from monocyclic aryl and bicyclic aryl and substituted with 0, 1, 2, or 3 groups independently selected from halogen, C1-C4 alkyl, C1-C4 alkylene, and C1-C4 alkoxy, in an amount of from about 20 wt % to about 60 wt %; and (c) a mixed ester composition in an amount of from about 10 wt % to about 30 wt %, wherein the mixed ester composition comprises a blend of: (i) a mixed ester having a structure represented by a formula:

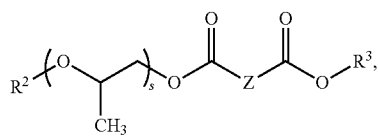

wherein s is an integer from 3 to 10; wherein Z is C4-C40 acyclic alkyl substituted with 0, 1, 2, or 3 independently selected C1-C10 alkylene groups; wherein $R^2$ is C4-C24 acyclic alkyl; and wherein $R^3$ is C4-C24 acyclic alkyl; and (ii) a wax component, thereby making the pre-blend composition.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including steps in methods of making and using the compositions of the invention. Thus, if there are a variety of additional steps that can be performed it is understood that each of these additional steps can be performed with any specific embodiment or combination of embodiments of the methods of the invention.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. Nothing herein is to be construed as an admission that the present invention is not entitled to antedate such publication by virtue of prior invention. Further, the dates of publication provided herein may be different from the actual publication dates, which can require independent confirmation.

A. Definitions

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

References to a composition containing "an" ingredient is intended to include other ingredients, respectively, in addition to the one named.

By "comprising" or "containing" or "having" it is intended that at least the named compound, element, particle, or method step, etc., is present in the composition or article or method, but does not exclude the presence of other compounds, catalysts, materials, particles, method steps, etc., even if the other such compounds, material, particles, method steps, etc., have the same function as what is named, unless expressly excluded in the claims.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "optional" or "optionally" means that the subsequently described event or circumstance may or may not occur, and that the description includes instances where said event or circumstance occurs and instances where it does not.

As used herein, the term "substantially" means that the subsequently described event or circumstance completely occurs or that the subsequently described event or circumstance generally, typically, or approximately occurs. For example, when the specification discloses that substantially all of an agent is released, a person skilled in the relevant art would readily understand that the agent need not be completely released. Rather, this term conveys to a person skilled in the relevant art that the agent need only be released to an extent that an effective amount is no longer unreleased.

As used herein, the term "cosmetic composition" refers to a product that may be applied to the skin or hair, including facial hair such as eye lashes) for the purpose of altering or enhancing appearance. Although such products may provide attributes such as cleansing, conditioning, or protection from UV radiation, the primary purpose of a cosmetic composition is to affect the feel and/or appearance of skin or hair after it is applied. Examples of cosmetic compositions include, but are not limited to, eye products (e.g., eyeshadows, eyeliners, and mascaras), nail lacquers, hair products (e.g., shampoos, conditioners, serums, and styling products), and a lip products (e.g., lipsticks, lip glosses, lip liners, lip plumpers, lip balms, lip sheers, lip inks, lip conditioners, lip primers, and lip boosters). In various aspects, a cosmetic composition has an acceptable pK value. For example, a cosmetic composition can have a pK of about 7.5 or about 7.5.17.

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as CHEMDRAW™ (Cambridgesoft Corporation, U.S.A.).

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —OCH$_2$CH$_2$O— units in the polyester, regardless of whether ethylene glycol was used to prepare the polyester. Similarly, a sebacic acid residue in a polyester refers to one or more —CO(CH$_2$)$_8$CO— moieties in the polyester, regardless of whether the residue is obtained by reacting sebacic acid or an ester thereof to obtain the polyester.

A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure

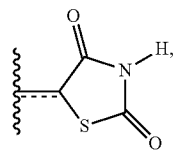

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

In some aspects, a structure of a compound can be represented by a formula:

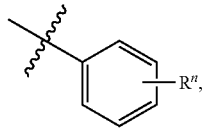

which is understood to be equivalent to a formula:

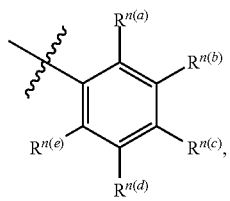

wherein n is typically an integer. That is, $R^n$ is understood to represent five independent substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance $R^{n(a)}$ is halogen, then $R^{n(b)}$ is not necessarily halogen in that instance.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

B. Pre-Blend Compositions

In one aspect, the invention relates to pre-blend compositions comprising: (a) a methyl phenyl silicone ester in an amount of from about 20 wt % to about 60 wt %; (b) an aromatic ester having a structure represented by a formula:

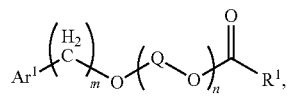

wherein m is an integer selected from 0 and 1; wherein n is an integer from 1 to 20; wherein each Q is independently C1-C6 acyclic alkyl; wherein $R^1$ is a C4-C24 acyclic alkyl; wherein $Ar^1$ is aryl substituted with 0, 1, 2, or 3 groups independently selected from halogen, C1-C4 alkyl, C1-C4 alkylene, C1-C4 alkoxy, —(C1-C8 alkyl)Ar², —SO₂Ar², and Ar²; and wherein Ar² is selected from monocyclic aryl and bicyclic aryl and substituted with 0, 1, 2, or 3 groups independently selected from halogen, C1-C4 alkyl, C1-C4 alkylene, and C1-C4 alkoxy, in an amount of from about 20 wt % to about 60 wt %; and (c) a mixed ester composition in an amount of from about 10 wt % to about 30 wt %, wherein the mixed ester composition comprises a blend of: (i) a mixed ester having a structure represented by a formula:

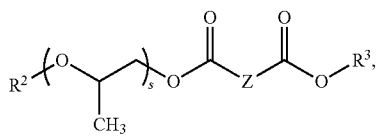

wherein s is an integer from 3 to 10; wherein Z is C4-C40 acyclic alkyl substituted with 0, 1, 2, or 3 independently selected C1-C10 alkylene groups; wherein R² is C4-C24 acyclic alkyl; and wherein R³ is C4-C24 acyclic alkyl; and (ii) a wax component.

The disclosed pre-blend compositions advantageously offer both a high shine and hydration and, accordingly, can be useful in the preparation of, for example, cosmetic compositions such as, for example, lip products. Additional benefits of the disclosed compositions and products made therefrom include, but are not limited to, improved pigment dispersion, minimal or no leeching, and reduced tackiness.

In a further aspect, the pre-blend composition comprises: (a) a methyl phenyl silicone ester in an amount of from about 30 wt % to about 50 wt %; (b) an aromatic ester having a structure represented by a formula:

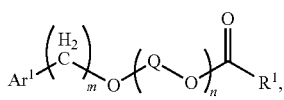

wherein m is an integer selected from 0 and 1; wherein n is an integer from 1 to 20; wherein each Q is independently C1-C6 acyclic alkyl; wherein R¹ is a C4-C24 acyclic alkyl; wherein Ar¹ is aryl substituted with 0, 1, 2, or 3 groups independently selected from halogen, C1-C4 alkyl, C1-C4 alkylene, C1-C4 alkoxy, —(C1-C8 alkyl)Ar², —SO₂Ar², and Ar²; and wherein Ar² is selected from monocyclic aryl and bicyclic aryl and substituted with 0, 1, 2, or 3 groups independently selected from halogen, C1-C4 alkyl, C1-C4 alkylene, and C1-C4 alkoxy, in an amount of from about 30 wt % to about 50 wt %; and (b) a mixed ester composition in an amount of from about 15 wt % to about 25 wt %, wherein the mixed ester composition comprises a blend of: (i) a mixed ester having a structure represented by a formula:

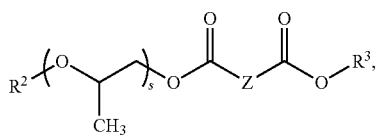

wherein s is an integer from 3 to 10; wherein Z is C4-C40 acyclic alkyl substituted with 0, 1, 2, or 3 independently selected C1-C10 alkylene groups; wherein R² is C4-C24 acyclic alkyl; and wherein R³ is C4-C24 acyclic alkyl; and (ii) a wax component.

In a further aspect, the pre-blend composition comprises: (a) a methyl phenyl silicone ester in an amount of about 40 wt %; (b) an aromatic ester having a structure represented by a formula:

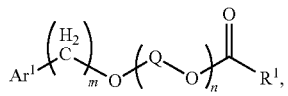

wherein m is an integer selected from 0 and 1; wherein n is an integer from 1 to 20; wherein each Q is independently C1-C6 acyclic alkyl; wherein R¹ is a C4-C24 acyclic alkyl; wherein Ar¹ is aryl substituted with 0, 1, 2, or 3 groups independently selected from halogen, C1-C4 alkyl, C1-C4 alkylene, C1-C4 alkoxy, —(C1-C8 alkyl)Ar², —SO₂Ar², and Ar²; and wherein Ar² is selected from monocyclic aryl and bicyclic aryl and substituted with 0, 1, 2, or 3 groups independently selected from halogen, C1-C4 alkyl, C1-C4 alkylene, and C1-C4 alkoxy, in an amount of about 40 wt %; and (b) a mixed ester composition in an amount of about 20 wt %, wherein the mixed ester composition comprises a blend of: (i) a mixed ester having a structure represented by a formula:

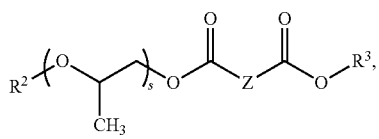

wherein s is an integer from 3 to 10; wherein Z is C4-C40 acyclic alkyl substituted with 0, 1, 2, or 3 independently selected C1-C10 alkylene groups; wherein R² is C4-C24 acyclic alkyl; and wherein R³ is C4-C24 acyclic alkyl; and (ii) a wax component.

In a further aspect, the methyl phenyl silicone ester is present in an amount of from about 30 wt % to about 60 wt %, the aromatic ester is present in an amount of from about 20 wt % to about 60 wt %, and the mixed ester composition is present in an amount of from about 10 wt % to about 30 wt %. In a still further aspect, In a further aspect, the methyl phenyl silicone ester is present in an amount of from about 40 wt % to about 60 wt %, the aromatic ester is present in an amount of from about 20 wt % to about 60 wt %, and the mixed ester composition is present in an amount of from about 10 wt % to about 30 wt %. In yet a further aspect, the methyl phenyl silicone ester is present in an amount of from about 20 wt % to about 50 wt %, the aromatic ester is present in an amount of from about 20 wt % to about 60 wt %, and the mixed ester composition is present in an amount of from about 10 wt % to about 30 wt %. In an even further aspect, the methyl phenyl silicone ester is present in an amount of from about 20 wt % to about 40 wt %, the aromatic ester is present in an amount of from about 20 wt % to about 60 wt %, and the mixed ester composition is present in an amount of from about 10 wt % to about 30 wt %. In a still further aspect, the methyl phenyl silicone ester is present in an amount of about 40 wt %, the aromatic ester is present in an amount of about 20 wt % to about 60 wt %, and the mixed ester composition is present in an amount of from about 10 wt % to about 30 wt %. In yet a further aspect, the methyl phenyl silicone ester is present in an amount of from about 20 wt % to about 60 wt %, the aromatic ester is present in an amount of from about 30 wt % to about 60 wt %, and the mixed ester composition is present in an amount of from about 10 wt % to about 30 wt %. In an even further aspect, the methyl phenyl silicone ester is present in an amount of from about 20 wt % to about 60 wt %, the aromatic ester is present in an amount of from about 40 wt % to about 60 wt %, and the mixed ester composition is present in an amount of from about 10 wt % to about 30 wt %. In a still further aspect, the methyl phenyl silicone ester is present in an amount of from about 20 wt % to about 60 wt %, the aromatic ester is present in an amount of from about 20 wt % to about 50 wt %, and the mixed ester composition is present in an amount of from about 10 wt % to about 30 wt %. In yet a further aspect, the methyl phenyl silicone ester is present in an amount of from about 20 wt % to about 60 wt %, the aromatic ester is present in an amount of from about 20 wt % to about 40 wt %, and the mixed ester composition is present in an amount of from about 10 wt % to about 30 wt %. In an even further aspect, the methyl phenyl silicone ester is present in an amount of from about 20 wt % to about 60 wt %, the aromatic ester is present in an amount of about 40 wt %, and the mixed ester composition is present in an amount of from about 10 wt % to about 30 wt %. In a still further aspect, the methyl phenyl silicone ester is present in an amount of from about 20 wt % to about 60 wt %, the aromatic ester is present in an amount of from about 20 wt % to about 60 wt %, and the mixed ester composition is present in an amount of from about 15 wt % to about 30 wt %. In yet a further aspect, the methyl phenyl silicone ester is present in an amount of from about 20 wt % to about 60 wt %, the aromatic ester is present in an amount of from about 20 wt % to about 60 wt %, and the mixed ester composition is present in an amount of from about 20 wt % to about 30 wt %. In an even further aspect, the methyl phenyl silicone ester is present in an amount of from about 20 wt % to about 60 wt %, the aromatic ester is present in an amount of from about 20 wt % to about 60 wt %, and the mixed ester composition is present in an amount of from about 10 wt % to about 25 wt %. In a still further aspect, the methyl phenyl silicone ester is present in an amount of from about 20 wt % to about 60 wt %, the aromatic ester is present in an amount of from about 20 wt % to about 60 wt %, and the mixed ester composition is present in an amount of from about 10 wt % to about 20 wt %. In yet a further aspect, the methyl phenyl silicone ester is present in an amount of from about 20 wt % to about 60 wt %, the aromatic ester is present in an amount of from about 20 wt % to about 60 wt %, and the mixed ester composition is present in an amount of about 20 wt %. In an even further aspect, the methyl phenyl silicone ester is present in an amount of about 40 wt %, the aromatic ester is present in an amount of about 40 wt %, and the mixed ester composition is present in an amount of about 20 wt %.

In a further aspect, the pre-blend composition comprises: (a) diphenylsiloxy phenyl trimethicone in an amount of from about 20 wt % to about 60 wt %; (b) PPG-3 benzyl ether myristate in an amount of from about 20 wt % to about 60 wt %; and (b) a mixed ester composition in an amount of from about 10 wt % to about 30 wt %, wherein the mixed ester composition comprises a blend of: (i) stearyl/PPG-3 myristyl ether dimer dilinoleate; and (ii) beeswax.

In a further aspect, the pre-blend composition comprises: (a) diphenylsiloxy phenyl trimethicone in an amount of from about 30 wt % to about 50 wt %; (b) PPG-3 benzyl ether myristate in an amount of from about 30 wt % to about 50 wt %; and (b) a mixed ester composition in an amount of from about 15 wt % to about 25 wt %, wherein the mixed ester composition comprises a blend of: (i) stearyl/PPG-3 myristyl ether dimer dilinoleate; and (ii) beeswax.

In a further aspect, the pre-blend composition comprises: (a) diphenylsiloxy phenyl trimethicone in an amount of about 40 wt %; (b) PPG-3 benzyl ether myristate in an amount of about 40 wt %; and (b) a mixed ester composition in an amount of about 20 wt %, wherein the mixed ester composition comprises a blend of: (i) stearyl/PPG-3 myristyl ether dimer dilinoleate; and (ii) beeswax.

In a further aspect, the methyl phenyl silicone ester is diphenylsiloxy phenyl trimethicone, the aromatic ester is PPG-3 benzyl ether myristate, and the mixed ester composition comprises stearyl/PPG-3 myristyl ether dimer dilinoleate and beeswax.

In a further aspect, the pre-blend is a shine complex suitable for use in a cosmetic composition.

1. Methyl Phenyl Silicone Esters

In one aspect, the pre-blend compositions of the present invention comprise a methyl phenyl silicone ester. Phenyl silicones such as methyl phenyl silicone esters are generally colorless transparent liquids. Moreover, these fluids offer a variety of beneficial properties including, but not limited to, low viscosity changes versus temperature, thermal stability, low flammability, shear stability, dielectric stability, high compressibility, chemical inertness, low surface tension, low toxicity, mold-releasability, water repellency, lubricity, defoaming properties, high refractive index, and shine.

The use of phenyl silicones in cosmetic composition is well established. For example, U.S. Pat. No. 5,556,613 discloses anhydrous silicone oil based-based cosmetic compositions containing a homogeneous fatty phase which contains phenyl substituted silicones that have repeating diphenyl silxoy or phenyl trimethylsiloxy moieties in combination with ethylene wax. U.S. Pat. No. 6,136,332 discloses transfer resistance of cosmetic compositions can be improved by incorporation of certain phenyl substituted silicones into the compositions. These phenyl substituted silicones contain either diphenylsiloxy or phenyltrimethylsiloxy repeating units.

Phenyl silicones can be purchased from a variety of commercial sources. For example, phenyl silicones can be purchased from Dow Corning (e.g., Dow Corning 555 Cosmetic Fluid having the INCI name trimethyl pentaphenyl trisiloxane), GE Silicones (e.g., SF 1555 having the INCI name bis-phenylpropyl dimethicone), Wacker-Belsil, General Electric, and Shin-Etsu (e.g., KF-56A having the INCI name diphenylsiloxy phenyl trimethicone).

In a further aspect, the methyl phenyl silicone ester has been approved for use in cosmetic compositions.

In a further aspect, the methyl phenyl silicone ester is present in an amount of from about 25 wt % to about 60 wt %. In a still further aspect, the methyl phenyl silicone ester is present in an amount of from about 30 wt % to about 60 wt %. In yet a further aspect, the methyl phenyl silicone ester is present in an amount of from about 35 wt % to about 60 wt %. In an even further aspect, the methyl phenyl silicone ester is present in an amount of from about 40 wt % to about 60 wt %. In a still further aspect, the methyl phenyl silicone ester is present in an amount of from about 45 wt % to about 60 wt %. In yet a further aspect, the methyl phenyl silicone ester is present in an amount of from about 50 wt % to about 60 wt %. In an even further aspect, the methyl phenyl silicone ester is present in an amount of from about 20 wt % to about 55 wt %. In yet a further aspect, the methyl phenyl silicone ester is present in an amount of from about 20 wt % to about 50 wt %. In an even further aspect, the methyl phenyl silicone ester is present in an amount of from about 20 wt % to about 45 wt %. In a still further aspect, the methyl phenyl silicone ester is present in an amount of from about 20 wt % to about 40 wt %. In yet a further aspect, the methyl phenyl silicone ester is present in an amount of from about 20 wt % to about 35 wt %. In an even further aspect, the methyl phenyl silicone ester is present in an amount of from about 20 wt % to about 30 wt %. In a still further aspect, the methyl phenyl silicone ester is present in an amount of from about 25 wt % to about 55 wt %. In yet a further aspect, the methyl phenyl silicone ester is present in an amount of from about 30 wt % to about 50 wt %. In an even further aspect, the methyl phenyl silicone ester is present in an amount of from about 35 wt % to about 45 wt %.

In a further aspect, the methyl phenyl silicone ester is present in an amount of about 20 wt %. In a still further aspect, the methyl phenyl silicone ester is present in an amount of about 25 wt %. In yet a further aspect, the methyl phenyl silicone ester is present in an amount of about 30 wt %. In an even further aspect, the methyl phenyl silicone ester is present in an amount of about 35 wt %. In a still further aspect, the methyl phenyl silicone ester is present in an amount of about 40 wt %. In yet a further aspect, the methyl phenyl silicone ester is present in an amount of about 45 wt %. In an even further aspect, the methyl phenyl silicone ester is present in an amount of about 50 wt %. In a still further aspect, the methyl phenyl silicone ester is present in an amount of about 55 wt %. In yet a further aspect, the methyl phenyl silicone ester is present in an amount of about 60 wt %.

In a further aspect, the methyl phenyl silicone ester has a refractive index of at least about 1.0. In a still further aspect, the methyl phenyl silicone ester has a refractive index of at least about 1.1. In yet a further aspect, the methyl phenyl silicone ester has a refractive index of at least about 1.2. In an even further aspect, the methyl phenyl silicone ester has a refractive index of at least about 1.3. In a still further aspect, the methyl phenyl silicone ester has a refractive index of at least about 1.35. In yet a further aspect, the methyl phenyl silicone ester has a refractive index of at least about 1.4. In an even further aspect, the methyl phenyl silicone ester has a refractive index of at least about 1.45. In a still further aspect, the methyl phenyl silicone ester has a refractive index of about 1.498.

In a further aspect, the methyl phenyl silicone ester is a straight silicone fluid. In a still further aspect, the methyl phenyl silicone ester is side chain-modified. In yet a further aspect, the methyl phenyl silicone ester is a non-reactive silicone fluid. In a still further aspect, the methyl phenyl silicone ester is diphenylsiloxy phenyl trimethicone.

2. Aromatic Esters

In one aspect, the pre-blend compositions of the present invention comprise an aromatic ester having a structure represented by a formula:

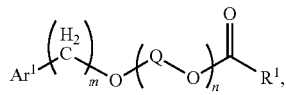

wherein m is an integer selected from 0 and 1; wherein n is an integer from 1 to 20; wherein each Q is independently C1-C6 acyclic alkyl; wherein R$^1$ is a C4-C24 acyclic alkyl; wherein Ar$^1$ is aryl substituted with 0, 1, 2, or 3 groups independently selected from halogen, C1-C4 alkyl, C1-C4 alkylene, C1-C4 alkoxy, —(C1-C8 alkyl)Ar$^2$, —SO$_2$Ar$^2$, and Ar$^2$; and wherein Ar$^2$ is selected from monocyclic aryl and bicyclic aryl and substituted with 0, 1, 2, or 3 groups independently selected from halogen, C1-C4 alkyl, C1-C4 alkylene, and C1-C4 alkoxy. Examples of aromatic esters having a structure as disclosed herein above include, but are not limited to, aromatic polyethylene glycol esters (i.e., PEG esters) and aromatic polypropylene glycol esters (i.e., PPG esters).

Aromatic esters are often used in cosmetic compositions as emollients, solubilizers, diluents, plastisizers, and/or thickeners. Such esters can provide various advantages to the composition such as, for example, a non-greasy feel, high solubility of UV filters, low skin-spreading factor, and good pigment wetting behavior. Moreover, the solubility of certain functional ingredients in cosmetic products can be enhanced by the presence of aromatic estters. Thus, in various aspects, aromatic esters can enhance shine (e.g., in hair products), enhance gloss (e.g., in lip products), and/or reduce the whitening effect of fatty alcohols and silica (e.g., in anti-perspirants and deodorants).

The disclosed aromatic esters can be prepared in a variety of methods known to one skilled in the art. See, e.g., U.S. Pat. Nos. 5,693,316, 5,597,555, 5,455,025, and 5,302,377. Typically, an aromatic ester as detailed herein can be prepared by esterification of an alkoxylated aromatic alcohol with a fatty carboxylic acid or a fatty carboxylic acid derivative such as, for example, an ester or an anhydride. Natural oils, synthetic oils, and triglycerides that contain fatty carboxylic groups may also be used.

Alkoxylated alcohols can be prepared via alkoxylation of the corresponding aromatic alcohol. The alkoxylation can be achieved by, for example, reacting the appropriate aromatic alcohol with an oxirane derivative in the presence of an appropriate base or acid, e.g., potassium hydroxide, sodium methoxide, sodium borohydride, boron trifluoride, stannic chloride, and sulfuric acid. Examples of alkoxylated alcohols include, but are not limited to, alkoxylated benzyl alcohol, alkoxylated phenoxyethanol, alkoxylated cynnamyl alcohol, alkoxylated phenoxy-n-propanol, and alkoxylated phenoxy-i-propanol, and mixtures thereof. Other non-limiting examples of suitable alkoxylated alcohols include alkoxylated bisphenol A, alkoxylated bisphenol AF, alkoxylated bisphenol AP, alkoxylated tetramethyl bisphenol A, alkoxylated bisphenol F, alkoxylated bisphenol E, alkoxylated bisphenol C, alkoxylated bisphenol M, alkoxylated bisphenol P, alkoxylated bisphenol S, alkoxylated bisphenol Z.

Fatty carboxylic acids and fatty carboxylic acid derivatives are commercially available or prepared by methods known to one of skill in the art. Examples of fatty carboxylic acids include, but are not limited to, myristic acid, propionic acid, capric acid, lauric acid, behenic acid, erucic acid, linoleic acid, montan acid, phenyl acetic acid, oleic acid, stearic acid, palmitic acid, coconut-oil-derived acid mixture, and palm oil-derived acid mixture, and mixtures thereof.

Alternatively, the disclosed aromatic esters can be commercially available. For example, PPG-3 benzyl ether myristate or Crodamol STS is available for purchase by Croda Inc. The key benefits of PPG-3 benzyl ether myristate include a silicone-like feel and functionality, improved emulsion aesthetics, ability to detackify popular emollients, enhanced gloss and shine, and ability to lessen the whitening effect of fatty alcohols. Other desirable properties include a high refractive, excellent wax solvency, it's easily emulsified, it acts as a foam stabilizer, and its' film-forming capabilites.

In a further aspect, the aromatic ester has been approved for use in cosmetic compositions.

In a further aspect, the aromatic ester has a structure represented by a formula:

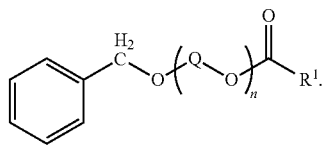

In a further aspect, the aromatic ester has a structure represented by a formula:

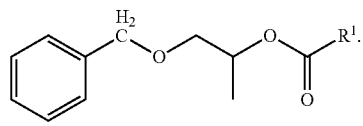

In a further aspect, the aromatic ester has a structure represented by a formula:

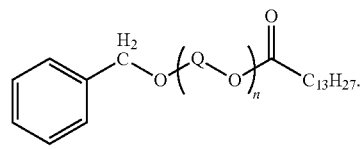

In a further aspect, the aromatic ester has a structure represented by a formula:

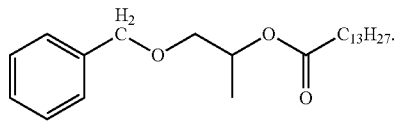

In a further aspect, m is an integer selected from 0 and 1. In a still further aspect, m is 0. In yet a further aspect, m is 1.

In a further aspect, n is an integer from 1-20. In a still further aspect, n is an integer selected from 1, 2, 3, 4, 5, 6, 7, 8, 9, 10, 11, 12, 13, 14, 15, 16, 17, 18, 19, and 20. In yet a further aspect, n is an integer from 1-15. In an even further aspect, n is an integer selected from 1, 2, 3, 4, 5, 6, 7, 8, 9, 10, 11, 12, 13, 14, and 15. In a still further aspect, n is an integer from 5-20. In yet a further aspect, n is an integer selected from 5, 6, 7, 8, 9, 10, 11, 12, 13, 14, 15, 16, 17, 18, 19, and 20. In an even further aspect, n is an integer from 5-15. In a still further aspect, n is an integer selected from 5, 6, 7, 8, 9, 10, 11, 12, 13, 14, and 15. In yet a further aspect, n is an integer from 10-15. In an even further aspect, n is an integer selected from 10, 11, 12, 13, 14, and 15. In a still further aspect, n is 10. In yet a further aspect, n is 11. In an even further aspect, n is 12. In a still further aspect, n is 13. In yet a further aspect, n is 14. In an even further aspect, n is 15.

In a further aspect, the aromatic ester is present in an amount of from about 25 wt % to about 60 wt %. In a still further aspect, the aromatic ester is present in an amount of from about 30 wt % to about 60 wt %. In yet a further aspect, the aromatic ester is present in an amount of from about 35 wt % to about 60 wt %. In an even further aspect, the aromatic ester is present in an amount of from about 40 wt % to about 60 wt %. In a still further aspect, the aromatic ester is present in an amount of from about 45 wt % to about 60 wt %. In yet a further aspect, the aromatic ester is present in an amount of from about 50 wt % to about 60 wt %. In an even further aspect, the aromatic ester is present in an amount of from about 20 wt % to about 55 wt %. In yet a further aspect, the aromatic ester is present in an amount of from about 20 wt % to about 50 wt %. In an even further aspect, the aromatic ester is present in an amount of from about 20 wt % to about 45 wt %. In a still further aspect, the aromatic ester is present in an amount of from about 20 wt % to about 40 wt %. In yet a further aspect, the aromatic ester is present in an amount of from about 20 wt % to about 35 wt %. In an even further aspect, the aromatic ester is present in an amount of from about 20 wt % to about 30 wt %. In a still further aspect, the aromatic ester is present in an amount of from about 25 wt % to about 55 wt %. In yet a further aspect, the aromatic ester is present in an amount of from about 30 wt % to about 50 wt %. In an even further aspect, the aromatic ester is present in an amount of from about 35 wt % to about 45 wt %.

In a further aspect, the aromatic ester is present in an amount of about 20 wt %. In a still further aspect, the aromatic ester is present in an amount of about 25 wt %. In yet a further aspect, the aromatic ester is present in an amount of about 30 wt %. In an even further aspect, the aromatic ester is present in an amount of about 35 wt %. In a still further aspect, the aromatic ester is present in an amount of about 40 wt %. In yet a further aspect, the aromatic ester is present in an amount of about 45 wt %. In an even further aspect, the aromatic ester is present in an amount of about 50 wt %. In a still further aspect, the aromatic ester is present in an amount of about 55 wt %. In yet a further aspect, the aromatic ester is present in an amount of about 60 wt %.

In a further aspect, the aromatic ester is PPG-3 benzyl ether myristate.

a. Q Groups

In one aspect, each Q is independently C1-C6 acyclic alkyl. In a further aspect, each Q is independently C1-C3 acyclic alkyl.

In a further aspect, each Q is independently selected from methyl, ethyl, n-propyl, propyl, n-butyl, i-butyl, s-butyl, and t-butyl. In a still further aspect, each Q is independently selected from methyl, ethyl, n-propyl, and i-propyl. In yet a further aspect, each Q is independently selected from methyl and ethyl. In an even further aspect, each Q is methyl. In a still further aspect, each Q is ethyl.

In a further aspect, each Q is independently selected from n-propyl and i-propyl. In a still further aspect, each Q is n-propyl. In a still further aspect, each Q is i-propyl.

b. $R^1$ Groups

In one aspect, $R^1$ is a C4-C24 acyclic alkyl. In a further aspect, $R^1$ is a C4-C22 acyclic alkyl. In a still further aspect, $R^1$ is a C4-C20 acyclic alkyl. In yet a further aspect, $R^1$ is a C4-C18 acyclic alkyl. In an even further aspect, $R^1$ is a C4-C16 acyclic alkyl. In a still further aspect, $R^1$ is a C4-C14 acyclic alkyl. In yet a further aspect, $R^1$ is a C4-C12 acyclic alkyl. In an even further aspect, $R^1$ is a C4-C10 acyclic alkyl. In an even further aspect, $R^1$ is a C4-C8 acyclic alkyl. In a still further aspect, $R^1$ is a C4-C6 acyclic alkyl. In yet a further aspect, $R^1$ is a C6-C24 acyclic alkyl. In an even further aspect, $R^1$ is a C8-C24 acyclic alkyl. In a still further aspect, $R^1$ is a C10-C24 acyclic alkyl. In yet a further aspect, $R^1$ is a C12-C24 acyclic alkyl. In an even further aspect, $R^1$ is a C14-C24 acyclic alkyl. In a still further aspect, $R^1$ is a C16-C24 acyclic alkyl. In yet a further aspect, $R^1$ is a C18-C24 acyclic alkyl. In an even further aspect, $R^1$ is a C20-C24 acyclic alkyl. In a still further aspect, $R^1$ is a C22-C24 acyclic alkyl. In yet a further aspect, $R^1$ is a C6-C22 acyclic alkyl. In an even further aspect, $R^1$ is a C8-C20 acyclic alkyl. In a still further aspect, $R^1$ is a C10-C18 acyclic alkyl. In yet a further aspect, $R^1$ is a C12-C16 acyclic alkyl.

In a further aspect, $R^1$ is a C4 acyclic alkyl. In a still further aspect, $R^1$ is a C5 acyclic alkyl. In yet a further aspect, $R^1$ is a C6 acyclic alkyl. In an even further aspect, $R^1$ is a C7 acyclic alkyl. In a still further aspect, $R^1$ is a C8 acyclic alkyl. In yet a further aspect, $R^1$ is a C9 acyclic alkyl. In an even further aspect, $R^1$ is a C10 acyclic alkyl. In a still further aspect, $R^1$ is a C11 acyclic alkyl. In yet a further aspect, $R^1$ is a C12 acyclic alkyl. In an even further aspect, $R^1$ is a C13 acyclic alkyl. In a still further aspect, $R^1$ is a C14 acyclic alkyl. In yet a further aspect, $R^1$ is a C15 acyclic alkyl. In an even further aspect, $R^1$ is a C16 acyclic alkyl. In a still further aspect, $R^1$ is a C17 acyclic alkyl. In yet a further aspect, $R^1$ is a C18 acyclic alkyl. In an even further aspect, $R^1$ is a C19 acyclic alkyl. In a still further aspect, $R^1$ is a C20 acyclic alkyl. In yet a further aspect, $R^1$ is a C21 acyclic alkyl. In an even further aspect, $R^1$ is a C22 acyclic alkyl. In a still further aspect, $R^1$ is a C23 acyclic alkyl. In yet a further aspect, $R^1$ is a C24 acyclic alkyl.

In a further aspect, $R^1$ is a C4-C24 linear acyclic alkyl. In a still further aspect, $R^1$ is a C4-C24 branched acyclic alkyl.

c. $Ar^1$ Groups

In one aspect, $Ar^1$ is aryl substituted with 0, 1, 2, or 3 groups independently selected from halogen, C1-C4 alkyl, C1-C4 alkylene, C1-C4 alkoxy, —(C1-C8 alkyl)$Ar^2$, —SO$_2$Ar$^2$, and $Ar^2$. In a further aspect, $Ar^1$ is aryl substituted with 0, 1, or 2 groups independently selected from halogen, C1-C4 alkyl, C1-C4 alkylene, C1-C4 alkoxy, —(C1-C8 alkyl)$Ar^2$, —SO$_2$Ar$^2$, and $Ar^2$. In a still further aspect, $Ar^1$ is aryl substituted with 0 or 1 group selected from halogen, C1-C4 alkyl, C1-C4 alkylene, C1-C4 alkoxy, —(C1-C8 alkyl)$Ar^2$, —SO$_2$Ar$^2$, and $Ar^2$. In yet a further aspect, $Ar^1$ is aryl monosubstituted with a group selected from halogen, C1-C4 alkyl, C1-C4 alkylene, C1-C4 alkoxy, —(C1-C8 alkyl)$Ar^2$, —SO$_2$Ar$^2$, and $Ar^2$. In an even further aspect, $Ar^1$ is unsubstituted aryl.

In a further aspect, $Ar^1$ is phenyl substituted with 0, 1, 2, or 3 groups independently selected from halogen, C1-C4 alkyl, C1-C4 alkylene, C1-C4 alkoxy, —(C1-C8 alkyl)$Ar^2$, —SO$_2$Ar$^2$, and $Ar^2$. In a still further aspect, $Ar^1$ is phenyl substituted with 0, 1, or 2 groups independently selected from halogen, C1-C4 alkyl, C1-C4 alkylene, C1-C4 alkoxy, —(C1-C8 alkyl)$Ar^2$, —SO$_2$Ar$^2$, and $Ar^2$. In yet a further aspect, $Ar^1$ is phenyl substituted with 0 or 1 group selected from halogen, C1-C4 alkyl, C1-C4 alkylene, C1-C4 alkoxy, —(C1-C8 alkyl)$Ar^2$, —SO$_2$Ar$^2$, and $Ar^2$. In an even further aspect, $Ar^1$ is phenyl monosubstituted with a group selected from halogen, C1-C4 alkyl, C1-C4 alkylene, C1-C4 alkoxy, —(C1-C8 alkyl)$Ar^2$, —SO$_2$Ar$^2$, and $Ar^2$. In a still further aspect, $Ar^1$ is unsubstituted phenyl.

d. $Ar^2$ Groups

In one aspect, $Ar^2$ is selected from monocyclic aryl and bicyclic aryl and substituted with 0, 1, 2, or 3 groups independently selected from halogen, C1-C4 alkyl, C1-C4 alkylene, and C1-C4 alkoxy. In a further aspect, $Ar^2$ is selected from monocyclic aryl and bicyclic aryl and substituted with 0, 1, or 2 groups independently selected from halogen, C1-C4 alkyl, C1-C4 alkylene, and C1-C4 alkoxy. In a still further aspect, $Ar^2$ is selected from monocyclic aryl and bicyclic aryl and substituted with 0 or 1 group selected from halogen, C1-C4 alkyl, C1-C4 alkylene, and C1-C4 alkoxy. In yet a further aspect, $Ar^2$ is selected from monocyclic aryl and bicyclic aryl and monosubstituted with a group selected from halogen, C1-C4 alkyl, C1-C4 alkylene, and C1-C4 alkoxy. In an even further aspect, $Ar^2$ is selected from monocyclic aryl and bicyclic aryl and unsubstituted.

In a further aspect, $Ar^2$ is monocyclic aryl substituted with 0, 1, 2, or 3 groups independently selected from halogen, C1-C4 alkyl, C1-C4 alkylene, and C1-C4 alkoxy. In a still further aspect, $Ar^2$ is monocyclic aryl substituted with 0, 1, or 2 groups independently selected from halogen, C1-C4 alkyl, C1-C4 alkylene, and C1-C4 alkoxy. In yet a further aspect, $Ar^2$ is monocyclic aryl substituted with 0 or 1 group selected from halogen, C1-C4 alkyl, C1-C4 alkylene, and C1-C4 alkoxy. In an even further aspect, $Ar^2$ is monocyclic aryl monosubstituted with a group selected from halogen, C1-C4 alkyl, C1-C4 alkylene, and C1-C4 alkoxy. In an even further aspect, $Ar^2$ is unsubstituted monocyclic aryl.

In a further aspect, $Ar^2$ is phenyl substituted with 0, 1, 2, or 3 groups independently selected from halogen, C1-C4 alkyl, C1-C4 alkylene, and C1-C4 alkoxy. In a still further aspect, $Ar^2$ is phenyl substituted with 0, 1, or 2 groups independently selected from halogen, C1-C4 alkyl, C1-C4 alkylene, and C1-C4 alkoxy. In yet a further aspect, $Ar^2$ is phenyl substituted with 0 or 1 group selected from halogen, C1-C4 alkyl, C1-C4 alkylene, and C1-C4 alkoxy. In an even further aspect, $Ar^2$ is phenyl monosubstituted with a group selected from halogen, C1-C4 alkyl, C1-C4 alkylene, and C1-C4 alkoxy. In an even further aspect, $Ar^2$ is unsubstituted phenyl.

In a further aspect, $Ar^2$ is bicyclic aryl substituted with 0, 1, 2, or 3 groups independently selected from halogen, C1-C4 alkyl, C1-C4 alkylene, and C1-C4 alkoxy. In a still further aspect, $Ar^2$ is bicyclic aryl substituted with 0, 1, or 2 groups independently selected from halogen, C1-C4 alkyl, C1-C4 alkylene, and C1-C4 alkoxy. In yet a further aspect, $Ar^2$ is bicyclic aryl substituted with 0 or 1 group selected from halogen, C1-C4 alkyl, C1-C4 alkylene, and C1-C4 alkoxy. In an even further aspect, $Ar^2$ is bicyclic aryl monosubstituted with a group selected from halogen, C1-C4 alkyl, C1-C4 alkylene, and C1-C4 alkoxy. In a still further aspect, $Ar^2$ is unsubstituted bicyclic aryl.

In a further aspect, $Ar^2$ is naphthyl substituted with 0, 1, 2, or 3 groups independently selected from halogen, C1-C4 alkyl, C1-C4 alkylene, and C1-C4 alkoxy. In a still further aspect, $Ar^2$ is naphthyl substituted with 0, 1, or 2 groups independently selected from halogen, C1-C4 alkyl, C1-C4 alkylene, and C1-C4 alkoxy. In yet a further aspect, $Ar^2$ is naphthyl substituted with 0 or 1 group selected from halogen, C1-C4 alkyl, C1-C4 alkylene, and C1-C4 alkoxy. In an even further aspect, $Ar^2$ is naphthyl monosubstituted with a group selected from halogen, C1-C4 alkyl, C1-C4 alkylene, and C1-C4 alkoxy. In a still further aspect, $Ar^2$ is unsubstituted naphthyl.

3. Mixed Ester Compositions

In one aspect, the pre-blend compositions of the present invention comprise a mixed ester composition. In a further aspect, the mixed ester composition comprises a blend of: (i) a mixed ester having a structure represented by a formula:

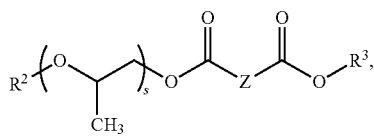

wherein s is an integer from 3 to 10; wherein Z is C4-C40 acyclic alkyl substituted with 0, 1, 2, or 3 independently selected C1-C10 alkylene groups; wherein $R^2$ is C4-C24 acyclic alkyl; and wherein $R^3$ is C4-C24 acyclic alkyl; and (ii) a wax component.

Mixed ester compositions have a range of beneficial properties. Examples of these benefits include, but are not limited to, providing softening to the skin, an enhanced barrier function, improving moisture retention, gloss, and wax compatibility. Moreover, these properties enable mixed ester compositions to serve a variety of functions in cosmetic compositions. For example, mixed ester compositions can function as an emollient, a glosser, a lubricant, a rheology modifier, and a thickener. In various aspects, the mixed ester composition can have little to no odor and a low melting point.

In a further aspect, the mixed ester composition has been approved for use in cosmetic compositions.

In a further aspect, the mixed ester composition is present in an amount of from about 10 wt % to about 30 wt %. In a still further aspect, the mixed ester composition is present in an amount of from about 15 wt % to about 30 wt %. In yet a further aspect, the mixed ester composition is present in an amount of from about 20 wt % to about 30 wt %. In an even further aspect, the mixed ester composition is present in an amount of from about 25 wt % to about 30 wt %. In a still further aspect, the mixed ester composition is present in an amount of from about 10 wt % to about 25 wt %. In yet a further aspect, the mixed ester composition is present in an amount of from about 10 wt % to about 20 wt %. In an even further aspect, the mixed ester composition is present in an amount of from about 10 wt % to about 15 wt %. In yet a further aspect, the mixed ester composition is present in an amount of from about 15 wt % to about 25 wt %.

In a further aspect, the mixed ester composition is present in an amount of about 10 wt %. In a still further aspect, the mixed ester composition is present in an amount of about 15 wt %. In yet a further aspect, the mixed ester composition is present in an amount of about 20 wt %. In an even further aspect, the mixed ester composition is present in an amount of about 25 wt %. In a still further aspect, the mixed ester composition is present in an amount of about 30 wt %.

In a further aspect, the mixed ester composition has a refractive index of at least about 1.0. In a still further aspect, the mixed ester composition has a refractive index of at least about 1.1. In yet a further aspect, the mixed ester composition has a refractive index of at least about 1.2. In an even further aspect, the mixed ester composition has a refractive index of at least about 1.3. In a still further aspect, the mixed ester composition has a refractive index of at least about 1.35. In yet a further aspect, the mixed ester composition has a refractive index of at least about 1.4. In an even further aspect, the mixed ester composition has a refractive index of at least about 1.45. In a still further aspect, the mixed ester composition has a refractive index of about 1.4720.

In a further aspect, the mixed ester composition comprises stearyl/PPG-3 myristyl ether dimer dilinoleate and beeswax. In yet a further aspect, the mixed ester composition consists essentially of stearyl/PPG-3 myristyl ether dimer dilinoleate and beeswax. In an even further aspect, the mixed ester composition is commercially available as Liquiwax™ PolyIPL (Croda, Inc.).

a. Mixed Esters

In one aspect, the mixed ester composition comprises a mixed ester having a structure represented by a formula:

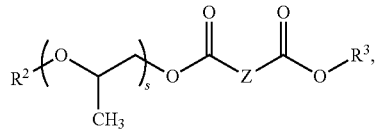

wherein s is an integer from 3 to 10; wherein Z is C4-C40 acyclic alkyl substituted with 0, 1, 2, or 3 independently selected C1-C10 alkylene groups; wherein $R^2$ is C4-C24 acyclic alkyl; and wherein $R^3$ is C4-C24 acyclic alkyl. Examples of mixed esters having a structure as disclosed herein above include, but are not limited to, stearyl/PPG-3 myristyl ether dimer dilinoleate.

In a further aspect, the mixed ester has a structure represented by a formula:

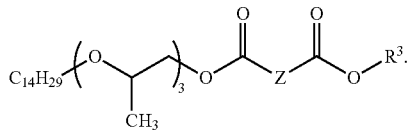

In a further aspect, the mixed ester has a structure represented by a formula:

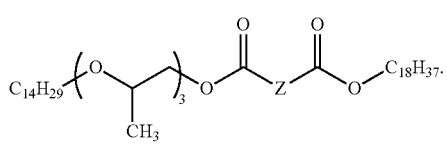

In a further aspect, the mixed ester has a structure represented by a formula:

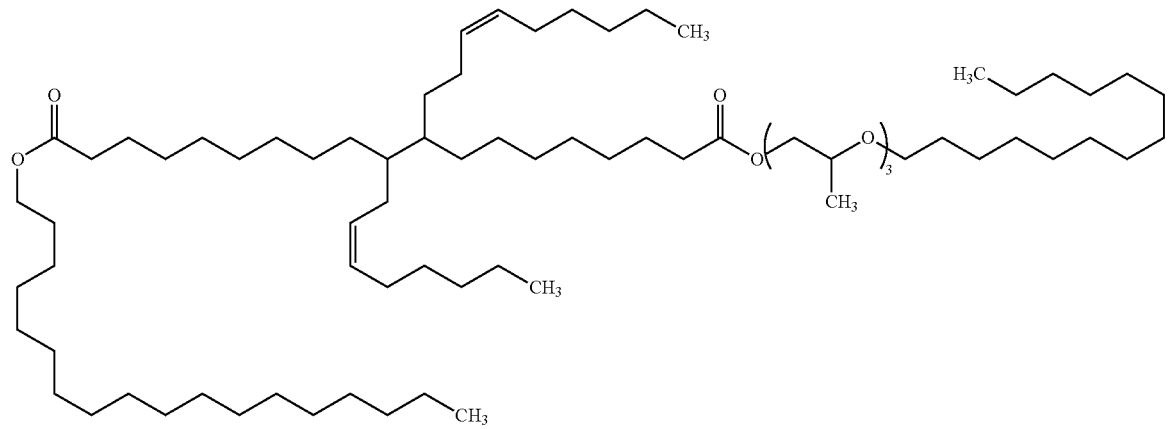

In a further aspect, s is an integer from 3 to 10. In a still further aspect, s is an integer selected from 3, 4, 5, 6, 7, 8, 9, and 10. In yet a further aspect, s is an integer from 3 to 8. In an even further aspect, s is an integer selected from 3, 4, 5, 6, 7, and 8. In a still further aspect, s is an integer selected from 3 to 6. In yet a further aspect, s is an integer selected from 3, 4, 5, and 6. In an even further aspect, s is an integer selected from 3 and 4. In a still further aspect, s is 4. In yet a further aspect, s is 3.

In a further aspect, the mixed ester is present in an amount of from about 90 wt % to about 99 wt % of the mixed ester composition. In a still further aspect, the mixed ester is present in an amount of from about 92 wt % to about 99 wt % of the mixed ester composition. In yet a further aspect, the mixed ester is present in an amount of from about 94 wt % to about 99 wt % of the mixed ester composition. In an even further aspect, the mixed ester is present in an amount of from about 96 wt % to about 99 wt % of the mixed ester composition. In a still further aspect, the mixed ester is present in an amount of from about 98 wt % to about 99 wt % of the mixed ester composition. In yet a further aspect, the mixed ester is present in an amount of from about 90 wt % to about 97 wt % of the mixed ester composition. In an even further aspect, the mixed ester is present in an amount of from about 90 wt % to about 95 wt % of the mixed ester composition. In yet a further aspect, the mixed ester is present in an amount of from about 90 wt % to about 93 wt % of the mixed ester composition.

In a further aspect, the mixed ester is present in an amount of about 90 wt % of the mixed ester composition. In a still further aspect, the mixed ester is present in an amount of about 91 wt % of the mixed ester composition. In yet a further aspect, the mixed ester is present in an amount of about 92 wt % of the mixed ester composition. In an even further aspect, the mixed ester is present in an amount of about 93 wt % of the mixed ester composition. In a still further aspect, the mixed ester is present in an amount of about 94 wt % of the mixed ester composition. In yet a further aspect, the mixed ester is present in an amount of about 95 wt % of the mixed ester composition. In an even further aspect, the mixed ester is present in an amount of about 96 wt % of the mixed ester composition. In a still further aspect, the mixed ester is present in an amount of about 97 wt % of the mixed ester composition. In yet a further aspect, the mixed ester is present in an amount of about 98 wt % of the mixed ester composition. In an even further aspect, the mixed ester is present in an amount of about 99 wt % of the mixed ester composition. In a still further aspect, the mixed ester is present in an amount of greater than about 99 wt % of the mixed ester composition.

i. Z Groups

In one aspect, Z is C4-C40 acyclic alkyl substituted with 0, 1, 2, or 3 independently selected C1-C10 alkylene groups. In a further aspect, Z is C4-C40 acyclic alkyl substituted with 0, 1, or 2 independently selected C1-C10 alkylene groups. In a still further aspect, Z is C4-C40 acyclic alkyl substituted with 0 or 1 C1-C10 alkylene group. In yet a further aspect, Z is C4-C40 acyclic alkyl monosubstituted with a C1-C10 alkylene group. In an even further aspect, Z is unsubstituted C4-C40 acyclic alkyl.

In a further aspect, Z is C4-C35 acyclic alkyl substituted with 0, 1, 2, or 3 independently selected C1-C10 alkylene groups. In a still further aspect, Z is C4-C30 acyclic alkyl substituted with 0, 1, 2, or 3 independently selected C1-C10 alkylene groups. In yet a further aspect, Z is C4-C25 acyclic alkyl substituted with 0, 1, 2, or 3 independently selected C1-C10 alkylene groups. In an even further aspect, Z is C4-C20 acyclic alkyl substituted with 0, 1, 2, or 3 independently selected C1-C10 alkylene groups. In a still further aspect, Z is C4-C15 acyclic alkyl substituted with 0, 1, 2, or 3 independently selected C1-C10 alkylene groups. In yet a further aspect, Z is C10-C40 acyclic alkyl substituted with 0, 1, 2, or 3 independently selected C1-C10 alkylene groups. In an even further aspect, Z is C15-C40 acyclic alkyl substituted with 0, 1, 2, or 3 independently selected C1-C10 alkylene groups. In a still further aspect, Z is C20-C40 acyclic alkyl substituted with 0, 1, 2, or 3 independently selected C1-C10 alkylene groups. In yet a further aspect, Z is C25-C40 acyclic alkyl substituted with 0, 1, 2, or 3 independently selected C1-C10 alkylene groups. In an even further aspect, Z is C30-C40 acyclic alkyl substituted with 0, 1, 2, or 3 independently selected C1-C10 alkylene groups. In a still further aspect, Z is C17 acyclic alkyl substituted with 0, 1, 2, or 3 independently selected C1-C10 alkylene groups.

In a further aspect, Z is C4-C40 acyclic alkyl substituted with 0, 1, 2, or 3 independently selected C3-C10 alkylene groups. In a still further aspect, Z is C4-C40 acyclic alkyl substituted with 0, 1, 2, or 3 independently selected C5-C10 alkylene groups. In yet a further aspect, Z is C4-C40 acyclic alkyl substituted with 0, 1, 2, or 3 independently selected C7-C10 alkylene groups. In an even further aspect, Z is C4-C40 acyclic alkyl substituted with 0, 1, 2, or 3 independently selected C1-C8 alkylene groups. In a still further aspect, Z is C4-C40 acyclic alkyl substituted with 0, 1, 2, or 3 independently selected C1-C6 alkylene groups. In yet a further aspect, Z is C4-C40 acyclic alkyl substituted with 0, 1, 2, or 3 independently selected C1-C4 alkylene groups. In an even further aspect, Z is C4-C40 acyclic alkyl substituted with 0, 1, 2, or 3 independently selected C8-C9 alkylene groups.

In a further aspect, Z is C4-C40 acyclic alkyl substituted with 2 independently selected C1-C10 alkylene groups. In a still further aspect, Z is C17 acyclic alkyl substituted with 2 independently selected C1-C10 alkylene groups. In yet a further aspect, Z is C17 acyclic alkyl substituted with 2 independently selected C8-C9 alkylene groups. In an even further aspect, Z is C17 acyclic alkyl substituted with one C8 alkylene group and one C9 alkylene group.

In a further aspect, Z is C4-C40 linear acyclic alkyl. In a still further aspect, Z is C4-C40 branched acyclic alkyl.

In a further aspect, Z is a structure:

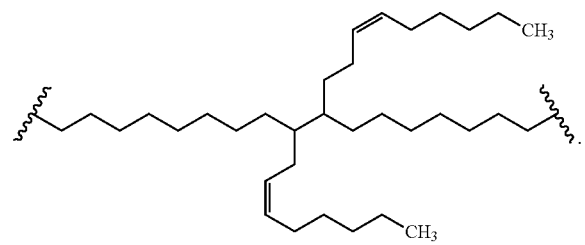 [SMILES: *CCCCCCCCC(C/C=C\CCCCC)C(CC/C=C\CCCCC)CCCCCCC*]

ii. $R^2$ Groups

In one aspect, $R^2$ is C4-C24 acyclic alkyl. In a further aspect, $R^2$ is C4-C22 acyclic alkyl. In a still further aspect, $R^2$ is C4-C20 acyclic alkyl. In yet a further aspect, $R^2$ is C4-C18 acyclic alkyl. In an even further aspect, $R^2$ is C4-C16 acyclic alkyl. In a still further aspect, $R^2$ is C4-C14 acyclic alkyl. In yet a further aspect, $R^2$ is C6-C24 acyclic alkyl. In an even further aspect, $R^2$ is C8-C24 acyclic alkyl. In a still further aspect, $R^2$ is C10-C24 acyclic alkyl. In yet a further aspect, $R^2$ is C14-C24 acyclic alkyl. In an even further aspect, $R^2$ is C6-C22 acyclic alkyl. In a still further aspect, $R^2$ is C8-C20 acyclic alkyl. In yet a further aspect, $R^2$ is C10-C18 acyclic alkyl. In an even further aspect, $R^2$ is C12-C16 acyclic alkyl. In a still further aspect, $R^2$ is C14 acyclic alkyl.

In a further aspect, $R^2$ is C4-C24 linear acyclic alkyl. In a still further aspect, $R^2$ is C4-C24 branched acyclic alkyl.

iii. $R^3$ Groups

In a further aspect, $R^3$ is C4-C24 acyclic alkyl. In a further aspect, $R^3$ is C4-C22 acyclic alkyl. In a still further aspect, $R^3$ is C4-C20 acyclic alkyl. In yet a further aspect, $R^3$ is C4-C18 acyclic alkyl. In an even further aspect, $R^3$ is C6-C24 acyclic alkyl. In a still further aspect, $R^3$ is C8-C24 acyclic alkyl. In yet a further aspect, $R^3$ is C10-C24 acyclic alkyl. In an even further aspect, $R^3$ is C14-C24 acyclic alkyl. In a still further aspect, $R^3$ is C16-C24 acyclic alkyl. In yet a further aspect, $R^3$ is C18-C24 acyclic alkyl. In an even further aspect, $R^3$ is C8-C22 acyclic alkyl. In a still further aspect, $R^3$ is C12-C20 acyclic alkyl. In yet a further aspect, $R^3$ is C14-C20 acyclic alkyl. In a still further aspect, $R^3$ is C16-C20 acyclic alkyl. In a still further aspect, $R^3$ is C18 acyclic alkyl.

b. Wax Component

In one aspect, the mixed ester composition comprises a wax component. Examples of wax components include, but are not limited to, beeswax, or blends of long alkyl chains having esters of fatty acids and long chain alcohols such as Carnauba and paraffin.

In a further aspect, the wax is present in an amount of from about 1 wt % to about 10 wt % of the mixed ester composition. In a still further aspect, the wax is present in an amount of from about 1 wt % to about 8 wt % of the mixed ester composition. In yet a further aspect, the wax is present in an amount of from about 1 wt % to about 6 wt % of the mixed ester composition. In an even further aspect, the wax is present in an amount of from about 1 wt % to about 4 wt % of the mixed ester composition. In a still further aspect, the wax is present in an amount of from about 1 wt % to about 2 wt % of the mixed ester composition. In yet a further aspect, the wax is present in an amount of from about 3 wt % to about 10 wt % of the mixed ester composition. In an even further aspect, the wax is present in an amount of from about 5 wt % to about 10 wt % of the mixed ester composition. In a still further aspect, the wax is present in an amount of from about 7 wt % to about 10 wt % of the mixed ester composition.

In a further aspect, the wax is present in an amount of about 1 wt % of the mixed ester composition. In a still further aspect, the wax is present in an amount of about 2 wt % of the mixed ester composition. In yet a further aspect, the wax is present in an amount of about 3 wt % of the mixed ester composition. In an even further aspect, the wax is present in an amount of about 4 wt % of the mixed ester composition. In a still further aspect, the wax is present in an amount of about 5 wt % of the mixed ester composition. In yet a further aspect, the wax is present in an amount of about 6 wt % of the mixed ester composition. In an even further aspect, the wax is present in an amount of about 7 wt % of the mixed ester composition. In a still further aspect, the wax is present in an amount of about 8 wt % of the mixed ester composition. In yet a further aspect, the wax is present in an amount of about 9 wt % of the mixed ester composition. In an even further aspect, the wax is present in an amount of about 10 wt % of the mixed ester composition.

C. Cosmetic Compositions

In one aspect, the invention relates to cosmetic compositions comprising: (a) a cosmetic base component comprising a disclosed pre-blend composition; (b) a first pigment; (c) an emollient; and (d) a long chain fatty alcohol. In a further aspect, the invention relates to cosmetic compositions comprising: (a) a cosmetic base component comprising a pre-blend composition comprising: (i) a methyl phenyl silicone ester in an amount of from about 20 wt % to about 60 wt %; (ii) an aromatic ester having a structure represented by a formula:

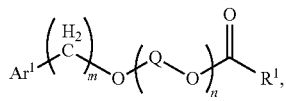

wherein m is an integer selected from 0 and 1; wherein n is an integer from 1 to 20; wherein each Q is independently C1-C6 acyclic alkyl; wherein $R^1$ is a C4-C24 acyclic alkyl; wherein $Ar^1$ is aryl substituted with 0, 1, 2, or 3 groups independently selected from halogen, C1-C4 alkyl, C1-C4 alkylene, C1-C4 alkoxy, —(C1-C8 alkyl)$Ar^2$, —$SO_2Ar^2$, and $Ar^2$; and wherein $Ar^2$ is selected from monocyclic aryl and bicyclic aryl and substituted with 0, 1, 2, or 3 groups independently selected from halogen, C1-C4 alkyl, C1-C4 alkylene, and C1-C4 alkoxy, in an amount of from about 20 wt % to about 60 wt %; and (iii) a mixed ester composition in an amount of from about 10 wt % to about 30 wt %, wherein the mixed ester composition comprises a blend of: (1) a mixed ester having a structure represented by a formula:

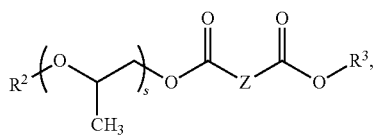

wherein s is an integer from 3 to 10; wherein Z is C4-C40 acyclic alkyl substituted with 0, 1, 2, or 3 independently selected C1-C10 alkylene groups; wherein $R^2$ is C4-C24 acyclic alkyl; and wherein $R^3$ is C4-C24 acyclic alkyl; and (2) a wax component.

The disclosed cosmetic compositions advantageously offer both a high shine and hydration, in addition to improved pigment dispersion, minimal or no leeching, and reduced tackiness. Examples of cosmetic compositions include, but are not limited to, eye products (e.g., eyeshadows, eyeliners, and mascaras), nail lacquers, hair products (e.g., shampoos, conditioners, serums, and styling products), and a lip products (e.g., lipsticks, lip glosses, lip liners, lip plumpers, lip balms, lip sheers, lip inks, lip conditioners, lip primers, and lip boosters).

In a further aspect, the cosmetic composition comprises: (a) a cosmetic base component comprising a disclosed pre-blend composition, wherein the cosmetic base is present in an amount of about 95 wt %; (b) a first pigment present in an amount of about 1.1 wt %; (c) an emollient in an amount of about 1.5 wt %; and (d) a long chain fatty acid in an amount of about 1.4 wt %.

In a further aspect, the cosmetic composition comprises: (a) a cosmetic base component comprising a disclosed pre-blend composition in an amount of from about 0.01 wt % to about 10 wt % of the cosmetic base component; (b) a first pigment; and (d) a long chain fatty acid. In a still further aspect, the cosmetic composition comprises: (a) a cosmetic base component comprising a disclosed pre-blend composition in an amount of from about 0.01 wt % to about 10 wt % of the cosmetic base component, wherein the cosmetic base is present in an amount of about 95 wt % of the cosmetic composition; (b) a first pigment present in an amount of about 1.1 wt %; (c) an emollient in an amount of about 1.5 wt %; and (d) a long chain fatty acid in an amount of about 1.4 wt %.

In a further aspect, the cosmetic composition comprises: (a) a cosmetic base component comprising a disclosed pre-blend composition; (b) a first pigment comprising a lake pigment; (c) an emollient; and (d) octyldodecanol.

In a further aspect, the cosmetic composition comprises: (a) a cosmetic base component comprising a disclosed pre-blend composition, wherein the cosmetic base is present in an amount of about 95 wt %; (b) a first pigment comprising a lake pigment, wherein the first pigment is present in an amount of about 1.1 wt %; (c) an emollient in an amount of about 1.5 wt %; and (d) octyldodecanol in an amount of about 1.4 wt %.

In a further aspect, the cosmetic composition is a stick-form.

In a further aspect, the cosmetic composition is selected from an eyeshadow, a mascara, a nail lacquer, a hair product, and a lip product. In a still further aspect, the cosmetic composition is a lip product.

In a further aspect, the cosmetic composition is a hot pour product. In a still further aspect, the cosmetic composition is a hot pour lip product.

1. Cosmetic Base Components

In one aspect, the cosmetic compositions of the present invention comprise a cosmetic base component comprising the disclosed pre-blend composition. In a further aspect, the cosmetic base component comprises a pre-blend composition comprising: (a) a methyl phenyl silicone ester in an amount of from about 20 wt % to about 60 wt %; (b) an aromatic ester having a structure represented by a formula:

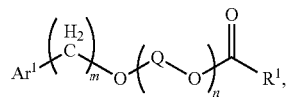

wherein m is an integer selected from 0 and 1; wherein n is an integer from 1 to 20; wherein each Q is independently C1-C6 acyclic alkyl; wherein $R^1$ is a C4-C24 acyclic alkyl; wherein $Ar^1$ is aryl substituted with 0, 1, 2, or 3 groups independently selected from halogen, C1-C4 alkyl, C1-C4 alkylene, C1-C4 alkoxy, —(C1-C8 alkyl)$Ar^2$, —$SO_2Ar^2$, and $Ar^2$; and wherein $Ar^2$ is selected from monocyclic aryl and bicyclic aryl and substituted with 0, 1, 2, or 3 groups independently selected from halogen, C1-C4 alkyl, C1-C4 alkylene, and C1-C4 alkoxy, in an amount of from about 20 wt % to about 60 wt %; and (c) a mixed ester composition in an amount of from about 10 wt % to about 30 wt %, wherein the mixed ester composition comprises a blend of: (i) a mixed ester having a structure represented by a formula:

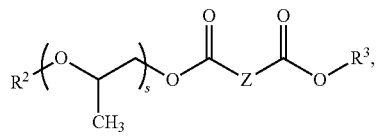

wherein s is an integer from 3 to 10; wherein Z is C4-C40 acyclic alkyl substituted with 0, 1, 2, or 3 independently selected C1-C10 alkylene groups; wherein $R^2$ is C4-C24 acyclic alkyl; and wherein $R^3$ is C4-C24 acyclic alkyl; and (ii) a wax component. In a still further aspect, the pre-blend is a shine complex suitable for use in a cosmetic composition.

In a further aspect, the cosmetic base component has been approved for use in cosmetic compositions.

In a further aspect, the cosmetic base component comprises a pre-blend composition comprising: (a) a methyl phenyl silicone ester in an amount of from about 30 wt % to about 50 wt %; (b) an aromatic ester having a structure represented by a formula:

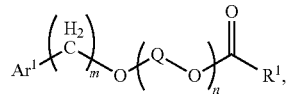

wherein m is an integer selected from 0 and 1; wherein n is an integer from 1 to 20; wherein each Q is independently C1-C6 acyclic alkyl; wherein $R^1$ is a C4-C24 acyclic alkyl; wherein $Ar^1$ is aryl substituted with 0, 1, 2, or 3 groups independently selected from halogen, C1-C4 alkyl, C1-C4 alkylene, C1-C4 alkoxy, —(C1-C8 alkyl)$Ar^2$, —$SO_2Ar^2$, and $Ar^2$; and wherein $Ar^2$ is selected from monocyclic aryl and bicyclic aryl and substituted with 0, 1, 2, or 3 groups independently selected from halogen, C1-C4 alkyl, C1-C4 alkylene, and C1-C4 alkoxy, in an amount of from about 30 wt % to about 50 wt %; and (c) a mixed ester composition in an amount of from about 15 wt % to about 25 wt %, wherein the mixed ester composition comprises a blend of: (i) a mixed ester having a structure represented by a formula:

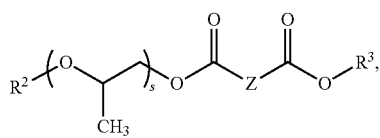

wherein s is an integer from 3 to 10; wherein Z is C4-C40 acyclic alkyl substituted with 0, 1, 2, or 3 independently selected C1-C10 alkylene groups; wherein $R^2$ is C4-C24 acyclic alkyl; and wherein $R^3$ is C4-C24 acyclic alkyl; and (ii) a wax component. In a still further aspect, the cosmetic base component comprises a pre-blend composition comprising: (a) a methyl phenyl silicone ester in an amount of about 40 wt %; (b) an aromatic ester having a structure represented by a formula:

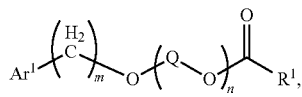

wherein m is an integer selected from 0 and 1; wherein n is an integer from 1 to 20; wherein each Q is independently C1-C6 acyclic alkyl; wherein $R^1$ is a C4-C24 acyclic alkyl; wherein $Ar^1$ is aryl substituted with 0, 1, 2, or 3 groups independently selected from halogen, C1-C4 alkyl, C1-C4 alkylene, C1-C4 alkoxy, —(C1-C8 alkyl)$Ar^2$, —$SO_2Ar^2$, and $Ar^2$; and wherein $Ar^2$ is selected from monocyclic aryl and bicyclic aryl and substituted with 0, 1, 2, or 3 groups independently selected from halogen, C1-C4 alkyl, C1-C4 alkylene, and C1-C4 alkoxy, in an amount of about 40 wt %; and (c) a mixed ester composition in an amount of about 20 wt %, wherein the mixed ester composition comprises a blend of: (i) a mixed ester having a structure represented by a formula:

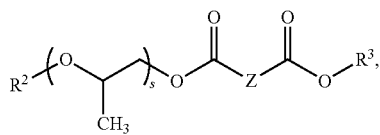

wherein s is an integer from 3 to 10; wherein Z is C4-C40 acyclic alkyl substituted with 0, 1, 2, or 3 independently selected C1-C10 alkylene groups; wherein $R^2$ is C4-C24 acyclic alkyl; and wherein $R^3$ is C4-C24 acyclic alkyl; and (ii) a wax component.

In a further aspect, the cosmetic base component comprises a pre-blend composition comprising: (a) diphenylsiloxy phenyl trimethicone in an amount of from about 20 wt % to about 60 wt %; (b) PPG-3 benzyl ether myristate in an amount of from about 20 wt % to about 60 wt %; and (b) a mixed ester composition in an amount of from about 10 wt % to about 30 wt %, wherein the mixed ester composition comprises a blend of: (i) stearyl/PPG-3 myristyl ether dimer dilinoleate; and (ii) beeswax. In a still further aspect, the cosmetic base component comprises a pre-blend composition comprising: (a) diphenylsiloxy phenyl trimethicone in an amount of from about 30 wt % to about 50 wt %; (b) PPG-3 benzyl ether myristate in an amount of from about 30 wt % to about 50 wt %; and (b) a mixed ester composition in an amount of from about 15 wt % to about 25 wt %, wherein the mixed ester composition comprises a blend of: (i) stearyl/PPG-3 myristyl ether dimer dilinoleate; and (ii) beeswax. In yet a further aspect, the cosmetic base component comprises a pre-blend composition comprising: (a) diphenylsiloxy phenyl trimethicone in an amount of about 40 wt %; (b) PPG-3 benzyl ether myristate in an amount of about 40 wt %; and (b) a mixed ester composition in an amount of about 20 wt %, wherein the mixed ester composition comprises a blend of: (i) stearyl/PPG-3 myristyl ether dimer dilinoleate; and (ii) beeswax.

In a further aspect, the cosmetic base component is present in an amount of from about 75 wt % to about 99 wt %. In a still further aspect, the cosmetic base component is present in an amount of from about 80 wt % to about 99 wt %. In yet a further aspect, the cosmetic base component is present in an amount of from about 85 wt % to about 99 wt %. In an even further aspect, the cosmetic base component is present in an amount of from about 90 wt % to about 99 wt %. In a still further aspect, the cosmetic base component is present in an amount of from about 95 wt % to about 99 wt %. In yet a further aspect, the cosmetic base component is present in an amount of from about 75 wt % to about 95 wt %. In an even further aspect, the cosmetic base component is present in an amount of from about 75 wt % to about 90 wt %. In yet a further aspect, the cosmetic base component is present in an amount of from about 75 wt % to about 85 wt %. In an even further aspect, the cosmetic base component is present in an amount of from about 75 wt % to about 80 wt %. In a still further aspect, the cosmetic base component is present in an amount of from about 90 wt % to about 97 wt %. In yet a further aspect, the cosmetic base component is present in an amount of from about 92 wt % to about 97 wt %. In an even further aspect, the cosmetic base component is present in an amount of from about 93 wt % to about 96 wt %.

In a further aspect, the cosmetic base component is present in an amount of about 90 wt %. In a still further aspect, the cosmetic base component is present in an amount of about 91 wt %. In yet a further aspect, the cosmetic base component is present in an amount of about 92 wt %. In an even further aspect, the cosmetic base component is present in an amount of about 93 wt %. In a still further aspect, the cosmetic base component is present in an amount of about 94 wt %. In yet a further aspect, the cosmetic base component is present in an amount of about 95 wt %. In an even further aspect, the cosmetic base component is present in an amount of about 96 wt %. In a still further aspect, the cosmetic base component is present in an amount of about 97 wt %. In yet a further aspect, the cosmetic base component is present in an amount of about 98 wt %. In an even further aspect, the cosmetic base component is present in an amount of about 99 wt %. In a still further aspect, the cosmetic base component is present in an amount of greater than about 99 wt %.

In a further aspect, the pre-blend composition is present in an amount of from about 0.01 wt % to about 10 wt % of the cosmetic base. In a still further aspect, the pre-blend composition is present in an amount of from about 0.1 wt % to about 10 wt % of the cosmetic base. In yet a further aspect, the pre-blend composition is present in an amount of from about 1 wt % to about 10 wt % of the cosmetic base. In an even further aspect, the pre-blend composition is present in an amount of from about 5 wt % to about 10 wt % of the cosmetic base. In a still further aspect, the pre-blend composition is present in an amount of from about 0.01 wt % to about 5 wt % of the cosmetic base. In yet a further aspect, the pre-blend composition is present in an amount of from about 0.01 wt % to about 1 wt % of the cosmetic base. In an even further aspect, the pre-blend composition is present in an amount of from about 0.01 wt % to about 0.1 wt % of the cosmetic base. In a still further aspect, the pre-blend composition is present in an amount of from about 1 wt % to about 5 wt % of the cosmetic base.

In a further aspect, the pre-blend composition comprises less than about 0.1 wt % of the cosmetic base. In a still further aspect, the pre-blend composition comprises about 0.1 wt % of the cosmetic base. In yet a further aspect, the pre-blend composition comprises about 1 wt % of the cosmetic base. In an even further aspect, the pre-blend composition comprises about 2 wt % of the cosmetic base. In a still further aspect, the pre-blend composition comprises about 3 wt % of the cosmetic base. In yet a further aspect, the pre-blend composition comprises about 4 wt % of the cosmetic base. In an even further aspect, the pre-blend composition comprises about 5 wt % of the cosmetic base. In a still further aspect, the pre-blend composition comprises about 6 wt % of the cosmetic base. In yet a further aspect, the pre-blend composition comprises about 7 wt % of the cosmetic base. In an even further aspect, the pre-blend composition comprises about 8 wt % of the cosmetic base. In a still further aspect, the pre-blend composition comprises about 9 wt % of the cosmetic base. In yet a further aspect, the pre-blend composition comprises about 10 wt % of the cosmetic base.

In a further aspect, the cosmetic base component comprises one or more of an emollient (e.g., dermol PIB H-100, elefac 1-205, dermol 99, dermol PETIS, dermol DISM), a film former (e.g., ganex V-216, polytrap 6603), a synthetic wax (e.g., Jeenate 5SW, Jeenate 4SW), a microcrystalline wax (e.g., microcrystalline wax SP18), lanolin or a lanolin substitute (e.g., softisan 649), an antimicrobial (e.g., Symdiol® 68), an adsorber, a sugar or artificial sweetener (e.g., syncal SDI-F), and a shine complex (e.g., a disclosed pre-blend composition).

2. Coloring Agents

In one aspect, the cosmetic compositions of the present invention comprise a coloring agent. Examples of coloring agents include, but are not limited to, pigments, dyes, shimmer, and pearls.

In a further aspect, the cosmetic compositions of the present invention comprise a first pigment. As used herein, the term "pigment" refers to an inorganic or organic agent that changes the color of reflected or transmitted light due to wavelength-selective absorption. Desirable properties of pigments include, but are not limited to, stability, high tinting strength, and permanence. Example of inorganic pigments include, but are not limited to, magnesium oxide, magnesium hydroxide, calcium oxide, calcium hydroxide, aluminum oxide, aluminum hydroxide, chromium oxide, chromium hydroxide, cobalt oxide, iron oxides, iron hydroxide, manganese oxides, nickel oxide, tin oxide, titanium dioxide, zirconium oxide, zinc oxide, and combinations thereof. Additional examples of inorganic pigments include ultramarine blue (i.e., sodium aluminum silicate containing sulfur), Prussian blue, manganese violet, sericite, potassium ferricyanide, potassium ferrocyanide, potassium ferrocyanide trihydrate, magnesium carbonate, calcium carbonate, silica, talc, mica, magnesium silicate, aluminum magnesium silicate, carbon black, and composite oxides and composite hydroxides such as iron titanate, cobalt titanate and cobalt aluminate, and combinations thereof. Examples of organic pigments include, but are not limited to, carmine, phthalocyanine blue and green pigment, diarylide yellow and orange pigments, and azo-type red and yellow pigments such as toluidine red, litho red, naphthol red and brown pigments, and combinations thereof.

In a further aspect, the first pigment has been approved for use in cosmetic compositions.

In a further aspect, the first pigment comprises a lake pigment. In a still further aspect, the first pigment comprises at least two lake pigments. As used herein, the term "lake pigment" refers to a colorant prepared from a water-soluble organic dye (e.g., D&C or FD&C) which has been precipitated onto an insoluble reactive or adsorptive substratum or diluent. The term "D&C" refers to drug and cosmetic colorants that are approved for use in drugs and cosmetics by the FDA. The term "FD&C" refers to food, drug, and cosmetic colorants which are approved for use in foods, drugs, and cosmetics by the FDA. Certified D&C and FD&C colorants are listed in 21 C.F.R. § 74.101 et seq. and include the FD&C colors Blue 1, Blue 2, Green 3, Orange B, Citrus Red 2, Red 3, Red 4, Red 40, Yellow 5, Yellow 6, Blue 1, Blue 2; Orange B, Citrus Red 2; and the D&C colors Blue 4, Blue 9, Green 5, Green 6, Green 8, Orange 4, Orange 5, Orange 10, Orange 11, Red 6, Red 7, Red 17, Red 21, Red 22, Red 27, Red 28, Red 30, Red 31, Red 33, Red 34, Red 36, Red 39, Violet 2, Yellow 7, Yellow 8, Yellow 10, Yellow 11, Blue 4, Blue 6, Green 5, Green 6, Green 8, Orange 4, Orange 5, Orange 10, Orange 11, and so on. Substrates suitable for forming lakes include, without limitation, mica, bismuth oxychloride, sericite, alumina, aluminum, copper, bronze, silver, calcium, zirconium, barium, and strontium, titanated mica, fumed silica, spherical silica, polymethylmethacrylate (PMMA), micronized Teflon, boron nitride, acrylate copolymers, aluminum silicate, aluminum starch octenylsuccinate, bentonite, calcium silicate, cellulose, chalk, corn starch, diatomaceous earth, fuller's earth, glyceryl starch, hectorite, hydrated silica, kaolin, magnesium aluminum silicate, magnesium trisilicate, maltodextrin, montmorillonite, microcrystalline cellulose, rice starch, silica, talc, mica, titanium dioxide, zinc laurate, zinc myristate, zinc rosinate, alumina, attapulgite, calcium carbonate, calcium silicate, dextran, nylon, silica silylate, silk powder, sericite, soy flour, tin oxide, titanium hydroxide, trimagnesium phosphate, walnut shell powder, and mixtures thereof. Suitable lakes include, without limitation, those of red dyes from the monoazo, disazo, fluoran, xanthene, or indigoid families, such as Red 4, 6, 7, 17, 21, 22, 27, 28, 30, 31, 33, 34, 36, and Red 40; lakes of yellow pyrazole, monoazo, fluoran, xanthene, quinoline, dyes or salt thereof, such as Yellow 5, 6, 7, 8, 10, and 11; lakes of violet dyes including those from the anthroquinone family, such as Violet 2, as well as lakes of orange dyes, including Orange 4, 5, 10, 11, and the like. Suitable Lakes of D&C and FD&C dyes are defined in 21 C.F.R. § 82.51.

In a further aspect, the first pigment is present in an amount of from about 0.01 wt % to about 5 wt %. In a still further aspect, the first pigment is present in an amount of from about 0.1 wt % to about 5 wt %. In yet a further aspect, the first pigment is present in an amount of from about 1 wt % to about 5 wt %. In an even further aspect, the first pigment is present in an amount of from about 3 wt % to about 5 wt %. In a still further aspect, the first pigment is present in an amount of from about 0.01 wt % to about 3 wt %. In yet a further aspect, the first pigment is present in an amount of from about 0.01 wt % to about 1 wt %. In an even further aspect, the first pigment is present in an amount of from about 0.01 wt % to about 0.1 wt %. In yet a further aspect, the first pigment is present in an amount of from about 0.1 wt % to about 3 wt %. In an even further aspect, the first pigment is present in an amount of from about 1 wt % to about 3 wt %. In a still further aspect, the first pigment is present in an amount of from about 0.1 wt % to about 1 wt %.

In a further aspect, the first pigment is present in an amount of less than about 0.01 wt %. In a still further aspect, the first pigment is present in an amount of about 0.1 wt %. In yet a further aspect, the first pigment is present in an amount of about 1.0 wt %. In an even further aspect, the first pigment is present in an amount of about 1.1 wt %. In a still further aspect, the first pigment is present in an amount of about 1.2 wt %. In yet a further aspect, the first pigment is present in an amount of about 1.3 wt %. In an even further aspect, the first pigment is present in an amount of about 1.4 wt %. In a still further aspect, the first pigment is present in an amount of about 1.5 wt %. In yet a further aspect, the first pigment is present in an amount of about 1.6 wt %. In an even further aspect, the first pigment is present in an amount of about 1.7 wt %. In a still further aspect, the first pigment is present in an amount of about 1.8 wt %. In yet a further aspect, the first pigment is present in an amount of about 1.9 wt %. In an even further aspect, the first pigment is present in an amount of about 2.0 wt %. In a still further aspect, the first pigment is present in an amount of about 3.0 wt %. In yet a further aspect, the first pigment is present in an amount of about 4.0 wt %. In an even further aspect, the first pigment is present in an amount of about 5.0 wt %.

In a further aspect, the cosmetic compositions of the present invention comprise a second pigment. In a still further aspect, the second pigment is a mineral-based pigment. As used herein, the term "mineral-based pigment" refers to a colorant prepared from a water-soluble organic dye insolubilized or fixed on to a mineral substrate by means of a cationic or anionic chemical compound.

In a further aspect, the second pigment is present in an amount of from about 0.01 wt % to about 5 wt %. In a still further aspect, the second pigment is present in an amount of from about 0.1 wt % to about 5 wt %. In yet a further aspect, the second pigment is present in an amount of from about 1 wt % to about 5 wt %. In an even further aspect, the second pigment is present in an amount of from about 3 wt % to about 5 wt %. In a still further aspect, the second pigment is present in an amount of from about 0.01 wt % to about 3 wt %. In yet a further aspect, the second pigment is present in an amount of from about 0.01 wt % to about 1 wt %. In an even further aspect, the second pigment is present in an amount of from about 0.01 wt % to about 0.1 wt %. In yet a further aspect, the second pigment is present in an amount of from about 0.1 wt % to about 3 wt %. In an even further aspect, the second pigment is present in an amount of from about 1 wt % to about 3 wt %. In a still further aspect, the second pigment is present in an amount of from about 0.1 wt % to about 1 wt %.

In a further aspect, the second pigment is present in an amount of less than about 0.01 wt %. In a still further aspect, the second pigment is present in an amount of about 0.1 wt %. In yet a further aspect, the second pigment is present in an amount of about 1.0 wt %. In an even further aspect, the second pigment is present in an amount of about 1.1 wt %. In a still further aspect, the second pigment is present in an amount of about 1.2 wt %. In yet a further aspect, the second pigment is present in an amount of about 1.3 wt %. In an even further aspect, the second pigment is present in an amount of about 1.4 wt %. In a still further aspect, the second pigment is present in an amount of about 1.5 wt %. In yet a further aspect, the second pigment is present in an amount of about 1.6 wt %. In an even further aspect, the second pigment is present in an amount of about 1.7 wt %. In a still further aspect, the second pigment is present in an amount of about 1.8 wt %. In yet a further aspect, the second pigment is present in an amount of about 1.9 wt %. In an even further aspect, the second pigment is present in an amount of about 2.0 wt %. In a still further aspect, the second pigment is present in an amount of about 3.0 wt %. In yet a further aspect, the second pigment is present in an amount of about 4.0 wt %. In an even further aspect, the second pigment is present in an amount of about 5.0 wt %.

3. Emollients

In various aspects, the cosmetic compositions of the present invention comprise an emollient. As used herein, the term "emollient" refers to an agent that acts to prevent water loss to the skin or hair when applied externally. Examples of emollients include, but are not limited to, cholesterol, squaline and fatty acids, castor oil, almond oil, oleic acid oleyl ester, caprylic triglyceride, capric triglyceride, ocryl dodecanol, cetearyl isonanoate, oleyl alcohol, dioctyl cyclohexane, isopropyl stearate, and isopropyl myristate fatty esters.

Emollients have a variety of properties that make them beneficial for use in cosmetic compositions including moisturization, conditioning, smoothing, and softening. They typically fall into one of three categories: hydrophilic emollients, lipophilic emollients, and silicone fluid emollients. Hydrophilic emollients, which are water soluble, include glycerin, sorbitol, and propylene glycol. These are commonly used in shampoos and other bath products. In contrast, lipophilic emollients, which are not soluble in water, include both non-polar (e.g., mineral oil, isoparaffin, and isohexadecane) and polar (e.g., natural oils such as Jojoba oil, Olive oil, and coconut oil, esters such as octyl palmitate, isopropyl stearate, isopropyl palmitate, and acohols such as octyl dodecanol) groups. Finally, silicone fluid emollients provide high slickness and include cyclomethicone and dimethicone.

In a further aspect, the emollient has been approved for use in cosmetic compositions.

In a further aspect, the emollient is present in an amount of from about 0.01 wt % to about 5 wt %. In a still further aspect, the emollient is present in an amount of from about 0.1 wt % to about 5 wt %. In yet a further aspect, the emollient is present in an amount of from about 1 wt % to about 5 wt %. In an even further aspect, the emollient is present in an amount of from about 1.5 wt % to about 5 wt %. In a still further aspect, the emollient is present in an amount of from about 3 wt % to about 5 wt %. In yet a further aspect, the emollient is present in an amount of from about 0.01 wt % to about 3 wt %. In an even further aspect, the emollient is present in an amount of from about 0.01 wt % to about 1.5 wt %. In yet a further aspect, the emollient is present in an amount of from about 0.01 wt % to about 1 wt %. In an even further aspect, the emollient is present in an amount of from about 0.01 wt % to about 0.1 wt %. In a still further aspect, the emollient is present in an amount of from about 0.1 wt % to about 3 wt %. In yet a further aspect, the emollient is present in an amount of from about 1 wt % to about 3 wt %.

In a further aspect, the emollient is present in an amount of less than about 0.01 wt %. In a still further aspect, the emollient is present in an amount of about 0.1 wt %. In yet a further aspect, the emollient is present in an amount of about 1.0 wt %. In an even further aspect, the emollient is present in an amount of about 1.1 wt %. In a still further aspect, the emollient is present in an amount of about 1.2 wt %. In yet a further aspect, the emollient is present in an amount of about 1.3 wt %. In an even further aspect, the emollient is present in an amount of about 1.4 wt %. In a still further aspect, the emollient is present in an amount of about 1.5 wt %. In yet a further aspect, the emollient is present in an amount of about 1.6 wt %. In an even further aspect, the emollient is present in an amount of about 1.7 wt %. In a still further aspect, the emollient is present in an amount of about 1.8 wt %. In yet a further aspect, the emollient is present in an amount of about 1.9 wt %. In an even further aspect, the emollient is present in an amount of about 2.0 wt %. In a still further aspect, the emollient is present in an amount of about 3.0 wt %. In yet a further aspect, the emollient is present in an amount of about 4.0 wt %. In an even further aspect, the emollient is present in an amount of about 5.0 wt %.

4. Long Chain Fatty Alcohols

In one aspect, the compositions of the present invention comprise a long chain fatty alcohol. As used herein, the term "long chain fatty alcohol" refers to a compound containing at least 16 carbon atoms, which may be linear or branched, saturated or unsaturated. For example, a long chain fatty alcohol can be a primary fatty alcohol having a linear and saturated chain including, but not limited to, behenyl alcohol, stearyl alcohol, arachidyl alcohol, lignoceryl alcohol, ceryl alcohol, montanyl alcohol, and octyldodecanol, and combinations thereof. In a further aspect, the long chain fatty acid is octyldodecanol.

Without wishing to be bound by theory, long chain fatty alcohols can function as a thickening agent, an emulsifier, a solvent, a fragrance, a lubricant, and/or as an emollient. Because of these uses, long chain fatty alcohols are commonly used in a variety of cosmetic applications including, but not limited to, lip products, eye products, facial products (e.g., foundations, and concealers), sunscreens, and anti-aging products.

In a further aspect, the long chain fatty alcohol has been approved for use in cosmetic compositions.

In a further aspect, the long chain fatty alcohol has a chain length of C16-C30. In a still further aspect, the long chain fatty alcohol has a chain length of C18-C30. In yet a further aspect, the long chain fatty alcohol has a chain length of C20-C30. In an even further aspect, the long chain fatty alcohol has a chain length of C16-C28. In a still further aspect, the long chain fatty alcohol has a chain length of C16-C26. In yet a further aspect, the long chain fatty alcohol has a chain length of C16-C24. In an even further aspect, the long chain fatty alcohol has a chain length of C16-C22. In a still further aspect, the long chain fatty alcohol has a chain length of C16-C20. In yet a further aspect, the long chain fatty alcohol has a chain length of C18-C28. In an even further aspect, the long chain fatty alcohol has a chain length of C18-C26. In a still further aspect, the long chain fatty alcohol has a chain length of C18-C24. In yet a further aspect, the long chain fatty alcohol has a chain length of C18-C22.

In a further aspect, the long chain fatty alcohol has a chain length of at least 16 carbons. In a still further aspect, the long chain fatty alcohol has a chain length of at least 18 carbons. In yet a further aspect, the long chain fatty alcohol has a chain length of at least 20 carbons. In an even further aspect, the long chain fatty alcohol has a chain length of at least 22 carbons. In a still further aspect, the long chain fatty alcohol has a chain length of at least 24 carbons.

In a further aspect, the long chain fatty alcohol has a chain length of 16 carbons. In a still further aspect, the long chain fatty alcohol has a chain length of 17 carbons. In yet a further aspect, the long chain fatty alcohol has a chain length of 18 carbons. In an even further aspect, the long chain fatty alcohol has a chain length of 19 carbons. In a still further aspect, the long chain fatty alcohol has a chain length of 20 carbons. In yet a further aspect, the long chain fatty alcohol has a chain length of 21 carbons. In an even further aspect, the long chain fatty alcohol has a chain length of 22 carbons. In a still further aspect, the long chain fatty alcohol has a chain length of 23 carbons. In yet a further aspect, the long chain fatty alcohol has a chain length of 24 carbons.

In a further aspect, the long chain fatty alcohol is linear. In a still further aspect, the long chain fatty alcohol is branched. In yet a further aspect, the long chain fatty alcohol is saturated. In an even further aspect, the long chain fatty alcohol is unsaturated.

In a further aspect, the long chain fatty alcohol is present in an amount of from about 0.01 wt % to about 5 wt %. In a still further aspect, the long chain fatty alcohol is present in an amount of from about 0.1 wt % to about 5 wt %. In yet a further aspect, the long chain fatty alcohol is present in an amount of from about 1 wt % to about 5 wt %. In an even further aspect, the long chain fatty alcohol is present in an amount of from about 1.5 wt % to about 5 wt %. In a still further aspect, the long chain fatty alcohol is present in an amount of from about 3 wt % to about 5 wt %. In yet a further aspect, the long chain fatty alcohol is present in an amount of from about 0.01 wt % to about 3 wt %. In an even further aspect, the long chain fatty alcohol is present in an amount of from about 0.01 wt % to about 1.5 wt %. In yet a further aspect, the long chain fatty alcohol is present in an amount of from about 0.01 wt % to about 1 wt %. In an even further aspect, the long chain fatty alcohol is present in an amount of from about 0.01 wt % to about 0.1 wt %. In a still further aspect, the long chain fatty alcohol is present in an amount of from about 0.1 wt % to about 3 wt %. In yet a further aspect, the long chain fatty alcohol is present in an amount of from about 1 wt % to about 3 wt %.

In a further aspect, the long chain fatty alcohol is present in an amount of less than about 0.01 wt %. In a still further aspect, the long chain fatty alcohol is present in an amount of about 0.1 wt %. In yet a further aspect, the long chain fatty alcohol is present in an amount of about 1.0 wt %. In an even further aspect, the long chain fatty alcohol is present in an amount of about 1.1 wt %. In a still further aspect, the long chain fatty alcohol is present in an amount of about 1.2 wt %. In yet a further aspect, the long chain fatty alcohol is present in an amount of about 1.3 wt %. In an even further aspect, the long chain fatty alcohol is present in an amount of about 1.4 wt %. In a still further aspect, the long chain fatty alcohol is present in an amount of about 1.5 wt %. In yet a further aspect, the long chain fatty alcohol is present in an amount of about 1.6 wt %. In an even further aspect, the long chain fatty alcohol is present in an amount of about 1.7 wt %. In a still further aspect, the long chain fatty alcohol is present in an amount of about 1.8 wt %. In yet a further aspect, the long chain fatty alcohol is present in an amount of about 1.9 wt %. In an even further aspect, the long chain fatty alcohol is present in an amount of about 2.0 wt %. In a still further aspect, the long chain fatty alcohol is present in an amount of about 3.0 wt %. In yet a further aspect, the long chain fatty alcohol is present in an amount of about 4.0 wt %. In an even further aspect, the long chain fatty alcohol is present in an amount of about 5.0 wt %.

5. Optional Components

In one aspect, the cosmetic composition further comprises at least one additive. Thus, in various aspects, the disclosed cosmetic compositions can optionally comprise other active and inactive ingredients typically associated with cosmetic and personal care products, including, but not limited to, excipients, fillers, emulsifying agents, antioxidants, surfactants, film formers, chelating agents, gelling agents, flavorants, thickeners, emollients, humectants, moisturizers, vitamins, sodium ascorbyl/cholesteryl phosphate, minerals, botanicals, viscosity and/or rheology modifiers, sunscreens, keratolytics, depigmenting agents, retinoids, hormonal compounds, alpha-hydroxy acids, trioxaundecanedioic acid, alpha-keto acids, anti-mycobacterial agents, antifungal agents, antimicrobials, antivirals, analgesics, lipidic compounds, anti-allergenic agents, H1 or H2 antihistamines, anti-inflammatory agents, anti-irritants, antineoplastics, immune system boosting agents, immune system suppressing agents, anti-acne agents, anesthetics, antiseptics, insect repellents, skin cooling compounds, skin protectants, skin penetration enhancers, exfollients, lubricants, fragrances, colorants, staining agents, depigmenting agents, hypopigmenting agents, preservatives, stabilizers, pharmaceutical agents, photostabilizing agents, and combinations thereof. All of these additives and many others and their use are well known in the art and do not require extensive discussion.

In a further aspect, the additive is selected from a sunscreen, a self-tanning agent, a pigment, an opacifying agent, a moisturizer, a film former, a thickening agent, an emulsifier, a conditioning agent, a deodorant, an emollient, a humectant, a softener, a lubricant, a penetrant, a plastisizer, a dispersant, a preservative, a buffer, a chelating agent, a foaming agent, a coupling agent, a protein, a salt, and an oil.

In a further aspect, the additive is present in an amount of from about 0.01 wt % to about 5 wt %. In a still further aspect, the additive is present in an amount of from about 0.1 wt % to about 5 wt %. In yet a further aspect, the additive is present in an amount of from about 1 wt % to about 5 wt %. In an even further aspect, the additive is present in an amount of from about 1.5 wt % to about 5 wt %. In a still further aspect, the additive is present in an amount of from about 3 wt % to about 5 wt %. In yet a further aspect, the additive is present in an amount of from about 0.01 wt % to about 3 wt %. In an even further aspect, the additive is present in an amount of from about 0.01 wt % to about 1.5 wt %. In yet a further aspect, the additive is present in an amount of from about 0.01 wt % to about 1 wt %. In an even further aspect, the additive is present in an amount of from about 0.01 wt % to about 0.1 wt %. In a still further aspect, the additive is present in an amount of from about 0.1 wt % to about 3 wt %. In yet a further aspect, the additive is present in an amount of from about 1 wt % to about 3 wt %.

In a further aspect, the additive is present in an amount of less than about 0.01 wt %. In a still further aspect, the additive is present in an amount of about 0.1 wt %. In yet a further aspect, the additive is present in an amount of about 1.0 wt %. In an even further aspect, the additive is present in an amount of about 1.1 wt %. In a still further aspect, the additive is present in an amount of about 1.2 wt %. In yet a further aspect, the additive is present in an amount of about 1.3 wt %. In an even further aspect, the additive is present in an amount of about 1.4 wt %. In a still further aspect, the additive is present in an amount of about 1.5 wt %. In yet a further aspect, the additive is present in an amount of about 1.6 wt %. In an even further aspect, the additive is present in an amount of about 1.7 wt %. In a still further aspect, the additive is present in an amount of about 1.8 wt %. In yet a further aspect, the additive is present in an amount of about 1.9 wt %. In an even further aspect, the additive is present in an amount of about 2.0 wt %. In a still further aspect, the additive is present in an amount of about 3.0 wt %. In yet a further aspect, the additive is present in an amount of about 4.0 wt %. In an even further aspect, the additive is present in an amount of about 5.0 wt %.

In a further aspect, the cosmetic composition further comprises a flavorant. The flavorant can comprise natural flavors, fruit flavors, aromatic flavors, drink flavors, food recipe flavors, candy flavors, floral flavors, or perfumes, spices, and aromas designed to evoke a specific place, or a combination thereof. Examples of flavorants include, but are not limited to, natural flavors, fruit flavors, aromatic flavors, floral flavors, or perfumes, spices, and aromas designed to evoke a specific place, or a combination thereof. In yet a further aspect, exemplary flavorant flavors include, but are not limited to, apple, cherry, green tea, cinnamon, clove, black tea, plum, mango, date, watermelon, coconut, pear, jasmine, peach, fennel, fragrant melon, lychee, mint, chocolate, coffee, cream, banana, almond, grape, strawberry, blueberry, blackberry, pine, kiwi, sapote, taro, lotus, pineapple, orange, lemon, melon, licorice, vanilla, rose, osmanthus, ginseng, spearmint, citrus, cucumber, honeydew, walnut, almond, and honey, or a combination thereof. In a further aspect, the flavorant is derived from any natural ingredient that is known to have a pleasant flavor.

In a further aspect, the flavorant is present in an amount of from about 0.01 wt % to about 5 wt %. In a still further aspect, the flavorant is present in an amount of from about 0.1 wt % to about 5 wt %. In yet a further aspect, the flavorant is present in an amount of from about 1 wt % to about 5 wt %. In an even further aspect, the flavorant is present in an amount of from about 1.5 wt % to about 5 wt %. In a still further aspect, the flavorant is present in an amount of from about 3 wt % to about 5 wt %. In yet a further aspect, the flavorant is present in an amount of from about 0.01 wt % to about 3 wt %. In an even further aspect, the flavorant is present in an amount of from about 0.01 wt % to about 1.5 wt %. In yet a further aspect, the flavorant is present in an amount of from about 0.01 wt % to about 1 wt %. In an even further aspect, the flavorant is present in an amount of from about 0.01 wt % to about 0.1 wt %. In a still further aspect, the flavorant is present in an amount of from about 0.1 wt % to about 3 wt %. In yet a further aspect, the flavorant is present in an amount of from about 1 wt % to about 3 wt %.

In a further aspect, the flavorant is present in an amount of less than about 0.01 wt %. In a still further aspect, the flavorant is present in an amount of about 0.1 wt %. In yet a further aspect, the flavorant is present in an amount of about 1.0 wt %. In an even further aspect, the flavorant is present in an amount of about 1.1 wt %. In a still further aspect, the flavorant is present in an amount of about 1.2 wt %. In yet a further aspect, the flavorant is present in an amount of about 1.3 wt %. In an even further aspect, the flavorant is present in an amount of about 1.4 wt %. In a still further aspect, the flavorant is present in an amount of about 1.5 wt %. In yet a further aspect, the flavorant is present in an amount of about 1.6 wt %. In an even further aspect, the flavorant is present in an amount of about 1.7 wt %. In a still further aspect, the flavorant is present in an amount of about 1.8 wt %. In yet a further aspect, the flavorant is present in an amount of about 1.9 wt %. In an even further aspect, the flavorant is present in an amount of about 2.0 wt %. In a still further aspect, the flavorant is present in an amount of about 3.0 wt %. In yet a further aspect, the flavorant is present in an amount of about 4.0 wt %. In an even further aspect, the flavorant is present in an amount of about 5.0 wt %.

6. Properties

In various aspects, the cosmetic compositions of the invention can have various properties that provide the superior functions of the compositions, including superior shine, reduced or minimal tackiness, reduced or minimal bleeding, hydration, and moisturization. It is also understood that the cosmetic compositions have other properties.

1. Shine

Shine can be expressed using, for example, a glossmeter or the human eye. The shine of the compositions of the present invention can be measured, for example, using a glossmeter or the human eye (e.g., via a survey, questionnaire, panelists, etc.). Thus, in various aspects, the cosmetic composition has enhanced shine relative to a substantially identical reference cosmetic composition in the absence of the pre-blend composition.

In a further aspect, the reference composition is a stick-form. In a still further aspect, the reference composition is a lip product. In yet a further aspect, the reference composition is a lip balm. In an even further aspect, the reference composition is a lip gloss.

ii. Pigment Dispersion

The amount of pigment dispersion can be expressed in terms of the intensity of the composition. If the pigment is not well dispersed, spots of pigments/streaks will be visible and a relatively higher percentage of pigment will be needed to get the same intensity. Thus, in various aspects, the cosmetic composition has enhanced pigment dispersion relative to a substantially identical reference cosmetic composition in the absence of the pre-blend composition. In a still further aspect, the cosmetic composition has at least 20% less streaks (i.e., spots of pigments) than a substantially identical reference cosmetic composition in the absence of the pre-blend composition. In yet a further aspect, the cosmetic composition has at least 15% less streaks (i.e., spots of pigments) than a substantially identical reference cosmetic composition in the absence of the pre-blend composition. In an even further aspect, the cosmetic composition has at least 10% less streaks (i.e., spots of pigments) than a substantially identical reference cosmetic composition in the absence of the pre-blend composition. In a still further aspect, the cosmetic composition has at least 5% less streaks (i.e., spots of pigments) than a substantially identical reference cosmetic composition in the absence of the pre-blend composition. In yet a further aspect, the cosmetic composition has at least 1% less streaks (i.e., spots of pigments) than a substantially identical reference cosmetic composition in the absence of the pre-blend composition. In a further aspect, the cosmetic composition has at least 0.5% less streaks (i.e., spots of pigments) than a substantially identical reference cosmetic composition in the absence of the pre-blend composition when. In a still further aspect, the cosmetic composition has at least 0.1% less streaks (i.e., spots of pigments) than a substantially identical reference cosmetic composition in the absence of the pre-blend composition.

In a further aspect, the reference composition is a stick-form. In a still further aspect, the reference composition is a lip product. In yet a further aspect, the reference composition is a lip balm. In an even further aspect, the reference composition is a lip gloss.

iii. Tackiness

The tackiness of the compositions of the present invention can be measured, for example, by physically evaluating the composition on a human palm and/or lip. Thus, in various aspects, the cosmetic composition has less tackiness relative to a substantially identical reference cosmetic composition in the absence of the pre-blend composition. In a still further aspect, the cosmetic composition is at least 10% less tacky than a substantially identical reference cosmetic composition in the absence of the pre-blend composition.

In a further aspect, the reference composition is a stick-form. In a still further aspect, the reference composition is a lip product. In yet a further aspect, the reference composition is a lip balm. In an even further aspect, the reference composition is a lip gloss.

D. Methods of Making a Cosmetic Composition

In one aspect, the invention relates to method of makings a cosmetic composition, the method comprising the step of combining: (a) a cosmetic base comprising a disclosed pre-blend composition; (b) a first pigment; (c) an emollient; and (d) a long chain fatty alcohol, thereby making the cosmetic composition. Examples of cosmetic compositions include, but are not limited to, eye products (e.g., eyeshadows, eyeliners, and mascaras), nail lacquers, hair products (e.g., shampoos, conditioners, serums, and styling products), and a lip products (e.g., lipsticks, lip glosses, lip liners, lip plumpers, lip balms, lip sheers, lip inks, lip conditioners, lip primers, and lip boosters).

In a further aspect, the invention relates to cosmetic compositions comprising: (a) a cosmetic base component comprising a pre-blend composition comprising: (i) a methyl phenyl silicone ester in an amount of from about 20 wt % to about 60 wt %; (ii) an aromatic ester having a structure represented by a formula:

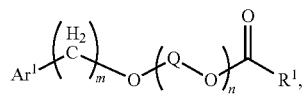

wherein m is an integer selected from 0 and 1; wherein n is an integer from 1 to 20; wherein each Q is independently C1-C6 acyclic alkyl; wherein $R^1$ is a C4-C24 acyclic alkyl; wherein $Ar^1$ is aryl substituted with 0, 1, 2, or 3 groups independently selected from halogen, C1-C4 alkyl, C1-C4 alkylene, C1-C4 alkoxy, —(C1-C8 alkyl)$Ar^2$, —$SO_2Ar^2$, and $Ar^2$; and wherein $Ar^2$ is selected from monocyclic aryl and bicyclic aryl and substituted with 0, 1, 2, or 3 groups independently selected from halogen, C1-C4 alkyl, C1-C4 alkylene, and C1-C4 alkoxy, in an amount of from about 20 wt % to about 60 wt %; and (iii) a mixed ester composition in an amount of from about 10 wt % to about 30 wt %, wherein the mixed ester composition comprises a blend of: (1) a mixed ester having a structure represented by a formula:

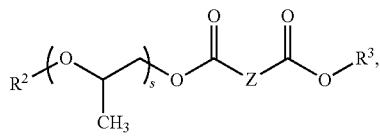

wherein s is an integer from 3 to 10; wherein Z is C4-C40 acyclic alkyl substituted with 0, 1, 2, or 3 independently selected C1-C10 alkylene groups; wherein $R^2$ is C4-C24 acyclic alkyl; and wherein $R^3$ is C4-C24 acyclic alkyl; and (2) a wax component.

In a further aspect, the cosmetic composition comprises: (a) a cosmetic base component comprising a disclosed pre-blend composition, wherein the cosmetic base is present in an amount of about 95 wt %; (b) a first pigment present in an amount of about 1.1 wt %; (c) an emollient in an amount of about 1.5 wt %; and (d) a long chain fatty acid in an amount of about 1.4 wt %.

In a further aspect, the cosmetic composition comprises: (a) a cosmetic base component comprising a disclosed pre-blend composition in an amount of from about 0.01 wt % to about 10 wt % of the cosmetic base component; (b) a first pigment; and (d) a long chain fatty acid. In a still further aspect, the cosmetic composition comprises: (a) a cosmetic base component comprising a disclosed pre-blend composition in an amount of from about 0.01 wt % to about 10 wt % of the cosmetic base component, wherein the cosmetic base is present in an amount of about 95 wt % of the cosmetic composition; (b) a first pigment present in an amount of about 1.1 wt %; (c) an emollient in an amount of about 1.5 wt %; and (d) a long chain fatty acid in an amount of about 1.4 wt %.

In a further aspect, the cosmetic composition comprises: (a) a cosmetic base component comprising a disclosed pre-blend composition; (b) a first pigment comprising a lake pigment; (c) an emollient; and (d) octyldodecanol.

In a further aspect, the cosmetic composition comprises: (a) a cosmetic base component comprising a disclosed pre-blend composition, wherein the cosmetic base is present in an amount of about 95 wt %; (b) a first pigment comprising a lake pigment, wherein the first pigment is present in an amount of about 1.1 wt %; (c) an emollient in an amount of about 1.5 wt %; and (d) octyldodecanol in an amount of about 1.4 wt %.

In a further aspect, the cosmetic composition is a stick-form.

In a further aspect, the cosmetic composition is selected from an eyeshadow, a mascara, a nail lacquer, a hair product, and a lip product. In a still further aspect, the cosmetic composition is a lip product.

In a further aspect, the cosmetic composition is a hot pour product. In a still further aspect, the cosmetic composition is a hot pour lip product.

In a further aspect, the method further comprises the step of combining a second pigment.

In a further aspect, the method further comprises the step of combining a flavorant.

E. Methods of Making a Pre-Blend Composition

In one aspect, the invention relates to methods of making a pre-blend composition, the method comprising the step of combining: (a) a methyl phenyl silicone ester in an amount of from about 20 wt % to about 60 wt %; (b) an aromatic ester having a structure represented by a formula:

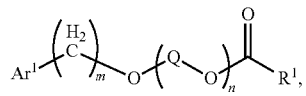

wherein m is an integer selected from 0 and 1; wherein n is an integer from 1 to 20; wherein each Q is independently C1-C6 acyclic alkyl; wherein $R^1$ is a C4-C24 acyclic alkyl; wherein $Ar^1$ is aryl substituted with 0, 1, 2, or 3 groups independently selected from halogen, C1-C4 alkyl, C1-C4 alkylene, C1-C4 alkoxy, —(C1-C8 alkyl)$Ar^2$, —$SO_2Ar^2$, and $Ar^2$; and wherein $Ar^2$ is selected from monocyclic aryl and bicyclic aryl and substituted with 0, 1, 2, or 3 groups independently selected from halogen, C1-C4 alkyl, C1-C4 alkylene, and C1-C4 alkoxy, in an amount of from about 20 wt % to about 60 wt %; and (c) a mixed ester composition in an amount of from about 10 wt % to about 30 wt %, wherein the mixed ester composition comprises a blend of: (i) a mixed ester having a structure represented by a formula:

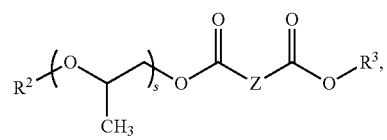

wherein s is an integer from 3 to 10; wherein Z is C4-C40 acyclic alkyl substituted with 0, 1, 2, or 3 independently selected C1-C10 alkylene groups; wherein $R^2$ is C4-C24 acyclic alkyl; and wherein $R^3$ is C4-C24 acyclic alkyl; and (ii) a wax component, thereby making the pre-blend composition.

In a further aspect, the pre-blend composition comprises: (a) a methyl phenyl silicone ester in an amount of from about 30 wt % to about 50 wt %; (b) an aromatic ester having a structure represented by a formula:

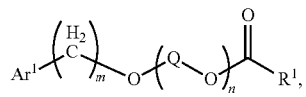

wherein m is an integer selected from 0 and 1; wherein n is an integer from 1 to 20; wherein each Q is independently C1-C6 acyclic alkyl; wherein $R^1$ is a C4-C24 acyclic alkyl; wherein $Ar^1$ is aryl substituted with 0, 1, 2, or 3 groups independently selected from halogen, C1-C4 alkyl, C1-C4 alkylene, C1-C4 alkoxy, —(C1-C8 alkyl)$Ar^2$, —$SO_2Ar^2$, and $Ar^2$; and wherein $Ar^2$ is selected from monocyclic aryl and bicyclic aryl and substituted with 0, 1, 2, or 3 groups independently selected from halogen, C1-C4 alkyl, C1-C4 alkylene, and C1-C4 alkoxy, in an amount of from about 30 wt % to about 50 wt %; and (b) a mixed ester composition in an amount of from about 15 wt % to about 25 wt %, wherein the mixed ester composition comprises a blend of: (i) a mixed ester having a structure represented by a formula:

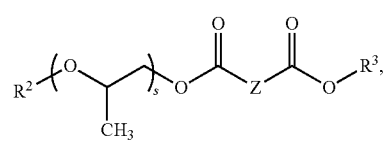

wherein s is an integer from 3 to 10; wherein Z is C4-C40 acyclic alkyl substituted with 0, 1, 2, or 3 independently selected C1-C10 alkylene groups; wherein $R^2$ is C4-C24 acyclic alkyl; and wherein $R^3$ is C4-C24 acyclic alkyl; and (ii) a wax component.

In a further aspect, the pre-blend composition comprises: (a) a methyl phenyl silicone ester in an amount of about 40 wt %; (b) an aromatic ester having a structure represented by a formula:

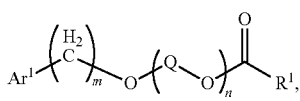

wherein m is an integer selected from 0 and 1; wherein n is an integer from 1 to 20; wherein each Q is independently C1-C6 acyclic alkyl; wherein $R^1$ is a C4-C24 acyclic alkyl; wherein $Ar^1$ is aryl substituted with 0, 1, 2, or 3 groups independently selected from halogen, C1-C4 alkyl, C1-C4 alkylene, C1-C4 alkoxy, —(C1-C8 alkyl)$Ar^2$, —$SO_2Ar^2$, and $Ar^2$; and wherein $Ar^2$ is selected from monocyclic aryl and bicyclic aryl and substituted with 0, 1, 2, or 3 groups independently selected from halogen, C1-C4 alkyl, C1-C4 alkylene, and C1-C4 alkoxy, in an amount of about 40 wt %; and (b) a mixed ester composition in an amount of about 20 wt %, wherein the mixed ester composition comprises a blend of: (i) a mixed ester having a structure represented by a formula:

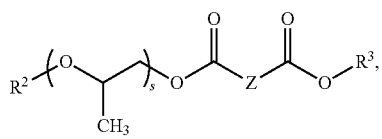

wherein s is an integer from 3 to 10; wherein Z is C4-C40 acyclic alkyl substituted with 0, 1, 2, or 3 independently selected C1-C10 alkylene groups; wherein $R^2$ is C4-C24 acyclic alkyl; and wherein $R^3$ is C4-C24 acyclic alkyl; and (ii) a wax component.

In a further aspect, the methyl phenyl silicone ester is present in an amount of from about 30 wt % to about 60 wt %, the aromatic ester is present in an amount of from about 20 wt % to about 60 wt %, and the mixed ester composition is present in an amount of from about 10 wt % to about 30 wt %. In a still further aspect, In a further aspect, the methyl phenyl silicone ester is present in an amount of from about 40 wt % to about 60 wt %, the aromatic ester is present in an amount of from about 20 wt % to about 60 wt %, and the mixed ester composition is present in an amount of from about 10 wt % to about 30 wt %. In yet a further aspect, the methyl phenyl silicone ester is present in an amount of from about 20 wt % to about 50 wt %, the aromatic ester is present in an amount of from about 20 wt % to about 60 wt %, and the mixed ester composition is present in an amount of from about 10 wt % to about 30 wt %. In an even further aspect, the methyl phenyl silicone ester is present in an amount of from about 20 wt % to about 40 wt %, the aromatic ester is present in an amount of from about 20 wt % to about 60 wt %, and the mixed ester composition is present in an amount of from about 10 wt % to about 30 wt %. In a still further aspect, the methyl phenyl silicone ester is present in an amount of about 40 wt %, the aromatic ester is present in an amount of from about 20 wt % to about 60 wt %, and the mixed ester composition is present in an amount of from about 10 wt % to about 30 wt %. In yet a further aspect, the methyl phenyl silicone ester is present in an amount of from about 20 wt % to about 60 wt %, the aromatic ester is present in an amount of from about 30 wt % to about 60 wt %, and the mixed ester composition is present in an amount of from about 10 wt % to about 30 wt %. In an even further aspect, the methyl phenyl silicone ester is present in an amount of from about 20 wt % to about 60 wt %, the aromatic ester is present in an amount of from about 40 wt % to about 60 wt %, and the mixed ester composition is present in an amount of from about 10 wt % to about 30 wt %. In a still further aspect, the methyl phenyl silicone ester is present in an amount of from about 20 wt % to about 60 wt %, the aromatic ester is present in an amount of from about 20 wt % to about 50 wt %, and the mixed ester composition is present in an amount of from about 10 wt % to about 30 wt %. In yet a further aspect, the methyl phenyl silicone ester is present in an amount of from about 20 wt % to about 60 wt %, the aromatic ester is present in an amount of from about 20 wt % to about 40 wt %, and the mixed ester composition is present in an amount of from about 10 wt % to about 30 wt %. In an even further aspect, the methyl phenyl silicone ester is present in an amount of from about 20 wt % to about 60 wt %, the aromatic ester is present in an amount of about 40 wt %, and the mixed ester composition is present in an amount of from about 10 wt % to about 30 wt %. In a still further aspect, the methyl phenyl silicone ester is present in an amount of from about 20 wt % to about 60 wt %, the aromatic ester is present in an amount of from about 20 wt % to about 60 wt %, and the mixed ester composition is present in an amount of from about 15 wt % to about 30 wt %. In yet a further aspect, the methyl phenyl silicone ester is present in an amount of from about 20 wt % to about 60 wt %, the aromatic ester is present in an amount of from about 20 wt % to about 60 wt %, and the mixed ester composition is present in an amount of from about 20 wt % to about 30 wt %. In an even further aspect, the methyl phenyl silicone ester is present in an amount of from about 20 wt % to about 60 wt %, the aromatic ester is present in an amount of from about 20 wt % to about 60 wt %, and the mixed ester composition is present in an amount of from about 10 wt % to about 25 wt %. In a still further aspect, the methyl phenyl silicone ester is present in an amount of from about 20 wt % to about 60 wt %, the aromatic ester is present in an amount of from about 20 wt % to about 60 wt %, and the mixed ester composition is present in an amount of from about 10 wt % to about 20 wt %. In yet a further aspect, the methyl phenyl silicone ester is present in an amount of from about 20 wt % to about 60 wt %, the aromatic ester is present in an amount of from about 20 wt % to about 60 wt %, and the mixed ester composition is present in an amount of about 20 wt %. In an even further aspect, the methyl phenyl silicone ester is present in an amount of about 40 wt %, the aromatic ester is present in an amount of about 40 wt %, and the mixed ester composition is present in an amount of about 20 wt %.

In a further aspect, the pre-blend composition comprises: (a) diphenylsiloxy phenyl trimethicone in an amount of from about 20 wt % to about 60 wt %; (b) PPG-3 benzyl ether myristate in an amount of from about 20 wt % to about 60 wt %; and (b) a mixed ester composition in an amount of from about 10 wt % to about 30 wt %, wherein the mixed ester composition comprises a blend of: (i) stearyl/PPG-3 myristyl ether dimer dilinoleate; and (ii) beeswax.

In a further aspect, the pre-blend composition comprises: (a) diphenylsiloxy phenyl trimethicone in an amount of from about 30 wt % to about 50 wt %; (b) PPG-3 benzyl ether myristate in an amount of from about 30 wt % to about 50 wt %; and (b) a mixed ester composition in an amount of from about 15 wt % to about 25 wt %, wherein the mixed ester composition comprises a blend of: (i) stearyl/PPG-3 myristyl ether dimer dilinoleate; and (ii) beeswax.

In a further aspect, the pre-blend composition comprises: (a) diphenylsiloxy phenyl trimethicone in an amount of about 40 wt %; (b) PPG-3 benzyl ether myristate in an amount of about 40 wt %; and (b) a mixed ester composition in an amount of about 20 wt %, wherein the mixed ester composition comprises a blend of: (i) stearyl/PPG-3 myristyl ether dimer dilinoleate; and (ii) beeswax.

In a further aspect, the methyl phenyl silicone ester is diphenylsiloxy phenyl trimethicone, the aromatic ester is PPG-3 benzyl ether myristate, and the mixed ester composition comprises stearyl/PPG-3 myristyl ether dimer dilinoleate and beeswax.

In a further aspect, the pre-blend is a shine complex suitable for use in a cosmetic composition.

F. Experimental

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. Preparation of a Pre-Blend Composition

A pre-blend composition was prepared having the formulation shown in Table 1 below. Briefly, the components of the pre-blend composition (i.e., KF-56A, Crodamol STS, and Liquiwax PolyIPL) were added to a suitable-sized kettle. Next, the components were mixed under medium-speed propeller agitation and heated to 95-98° C. Finally, the components continued to be mixed for approximately five minutes until they were uniform, ensuring that all waxes were melted.

TABLE 1

| Trade Name | INCI | Function | wt % |
| --- | --- | --- | --- |
| KF-56A | Diphenylsiloxy phenyl trimethicone | Skin-condition agent, miscellaneous | 40 |
| Crodamol STS | PPG-3 benzyl ether myristate | Skin-conditioning agent, emollient | 40 |
| Liquiwax PolyIPL | Stearyl/PPG-3 myristyl ether dimer dilinoleate (95%), Beeswax (5%) | Skin-condition agent, occlusive, miscellaneous | 20 |

2. Preparation of the Cosmetic Base Component

A cosmetic base component was prepared using the pre-blend composition detailed above and having the formulation shown in Table 2 below. Briefly, the pre-blend composition, Dermol DISM, Dermol PIB H-100, Ganex V-216, Jeenate 5SW, Jeenate 4SW, Microcrystalline wax SP18, Softisan 649, Elefac 1-205, Dermol 99, Symdiol 68, Dermol PETIS were added to a suitable sized main vessel. The components were mixed under medium-speed propeller agitation at 150 rpm and heated to 95-98° C. The components continued to be mixed for approximately fifteen minutes until they were uniform, ensuring that all waxes were melted. A small portion of base was dropped and combined with Syncal SDI-F under rollermill. The dropped out portion was then passed through the rollermill 2-3 passes or until the Syncal SDI-F was well-dispersed. Once uniform, the dropped out portion was charged back t the main vessel under propeller agitation and mixed until uniform. The sample was then poured at 95-98° C. and submitted to the IC lab for evaluation.

TABLE 2

| Trade Name | INCI Ingredient Name(s) | Function | wt % |
| --- | --- | --- | --- |
| Dermol DISM | Diisostearyl malate (92%), isostearyl alcohol (8%) | emollient | 22.8 |
| Dermol PIB H-100 | Polybutene | binder | 18.9 |
| Ganex V-216 | VP/Hexadecene copolymer | binder | 5.5 |
| Jeenate 5SW | Synthetic wax | binder | 5.1 |
| Jeenate 4SW | Synthetic wax | Binder | 1.6 |
| Microcrystalline wax SP18 | Microcrystalline wax | Viscosity increasing agents, nonaqueous | 2.9 |
| Softisan 649 | Bis-diglyceryl polyacyladipate-2 | Skin-conditioning agents, emollient | 7.9 |
| Elefac I-205 | Octyldodecyl neopentanoate (95.5%), octyldodecyl alcohol (4%), neopentanoic acid (0.5%) | Skin-conditioning agents, emollient | 11.9 |
| Dermol 99 | Isononyl isononanoate | Skin-conditioning agents, emollient | 4.7 |
| Symdiol 68 | 1,2-hexanediol (50%), caprylyl glycol (50%) | Skin-conditioning agents | 0.56 |
| Dermol PETIS | Pentaerythrityl tetraisostearate | Binder | 12 |
| Polytrap 6603 | Lauryl methacrylate/glycol dimethacrylate crosspolymer | Film-former | 0.56 |
| Pre-blend composition | Diphenylsiloxy phenyl trimethicone (40%), PPG-3 benzyl ether myristate (40%), Stearyl/PPG-3 myristyl ether dimer dilinoleate and Beeswax (20%) | See Table 1 above. | 5.5 |
| Syncal SDI-F | Saccharin (98%), water (2%) | Flavoring agent, solvent | 0.53 |

3. Preparation of a Cosmetic Composition

A cosmetic composition was prepared using the cosmetic base component detailed above and having the formulation shown in Table 3 below. Briefly, the complete base from Tables 1 and 2 was added into a suitable sized main vessel and heated to 85-95° C. The pigments or grinds were then added and the composition was propeller mixed slowly until unfirm. Finally, the temperature was dropped to below 70° C. and the flavor added.

TABLE 3

| Trade Name | INCI | Function | wt % |
|---|---|---|---|
| Cosmetic base | N/A | N/A | 95 |
| Red #28 Lake LC328/Eutanol G #25201 | Red 28 Lake (CI 45410), octyldodecanol | Colorant, skin-conditioning agent, emollient | 0.88 |
| Red #7 Lake LC3075/Eutanol G #25195 | Red 7 lake (CI 15850), octyldodecanol | Colorant, skin-conditioning agent, emollient | 1.1 |
| Mearlmica DD | Mica | Bulking agent | 0.01 |
| FLAV Sour Cherry Chili #FY6218 Flavor | N/A | Flavoring agent | 1.0 |
| Dermocol I-20 | Octyl Dodecanol | Skin-conditioning agent, emollient | 1.4 |

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A composition consisting of:
 (a) diphenylsiloxy phenyl trimethicone;
 (b) PPG-3 benzyl ether myristate; and
 (c) a mixed ester composition consisting of a blend of:
  (i) stearyl/PPG-3 myristyl ether dimer dilinoleate; and
  (ii) a wax component.

2. The composition of claim 1, wherein the wax is beeswax.

3. A composition consisting of:
 (a) diphenylsiloxy phenyl trimethicone in an amount of from 35 wt % to 45 wt %;
 (b) PPG-3 benzyl ether myristate in an amount of from 35 wt % to 45 wt %; and
 (c) a mixed ester composition in an amount of from 15 wt % to 25 wt %, wherein the mixed ester composition consists of:
  (i) stearyl/PPG-3 myristyl ether dimer dilinoleate; and
  (ii) a wax component.

4. The composition of claim 3, wherein the wax is beeswax.

5. The composition of claim 1, wherein diphenylsiloxy phenyl trimethicone is present in an amount of 40 wt %.

6. The composition of claim 1, wherein PPG-3 benzyl ether myristate is present in an amount of 40 wt %.

7. The composition of claim 1, wherein the mixed ester composition is present in an amount of 20 wt %.

8. The composition of claim 3, wherein diphenylsiloxy phenyl trimethicone is present in an amount of 40 wt %.

9. The composition of claim 3, wherein PPG-3 benzyl ether myristate is present in an amount of 40 wt %.

10. The composition of claim 3, wherein the mixed ester composition is present in an amount of 20 wt %.

11. The composition of claim 1, wherein the composition is present in a cosmetic composition.

12. The composition of claim 11, wherein the cosmetic composition is a lip cosmetic composition.

13. The composition of claim 3, wherein the composition is present in a cosmetic composition.

14. The composition of claim 13, wherein the cosmetic composition is a lip cosmetic composition.

15. A method of making a cosmetic composition, the method comprising combining:
 (a) the composition of claim 1,
 (b) a first pigment;
 (c) an emollient; and
 (d) a long chain fatty alcohol,
thereby making the cosmetic composition.

16. The method of claim 15, wherein the composition of claim 1 consists of:
 (a) diphenylsiloxy phenyl trimethicone in an amount of from 35 wt % to 45 wt %;
 (b) PPG-3 benzyl ether myristate in an amount of from 35 wt % to 45 wt %; and
 (c) a mixed ester composition in an amount of from 15 wt % to 25 wt %, wherein the mixed ester composition consists of a blend of:
  (i) stearyl/PPG-3 myristyl ether dimer dilinoleate; and
  (ii) a wax component.

17. The method of claim 16, wherein diphenylsiloxy phenyl trimethicone is present in an amount of 40 wt %.

18. The method of claim 16, wherein PPG-3 benzyl ether myristate is present in an amount of 40 wt %.

19. The method of claim 16, wherein the mixed ester composition is present in an amount of 20 wt %.

20. The method of claim 16, wherein the wax is beeswax.

21. The method of claim 16, wherein the cosmetic composition is a lip cosmetic composition.

22. The method of claim 16, further comprising combining a second pigment.

23. The method of claim 16, further comprising combining a flavorant.

24. A method of making a composition, the method consisting of combining:
 (a) diphenylsiloxy phenyl trimethicone;
 (b) PPG-3 benzyl ether myristate; and
 (c) a mixed ester composition consisting of a blend of:
  (iii) stearyl/PPG-3 myristyl ether dimer dilinoleate; and
  (iv) a wax component.

25. The method of claim 24, wherein:
 (a) the diphenylsiloxy phenyl trimethicone is in an amount of from 35 wt % to 45 wt %;
 (b) the PPG-3 benzyl ether myristate is in an amount of from 35 wt % to 45 wt %; and
 (c) the mixed ester composition is in an amount of from 15 wt % to 25 wt %, and wherein the mixed ester composition consists of a blend of:
  (i) stearyl/PPG-3 myristyl ether dimer dilinoleate; and
  (ii) a wax component.

26. The method of claim 25, wherein diphenylsiloxy phenyl trimethicone is present in an amount of 40 wt %.

27. The method of claim 25, wherein PPG-3 benzyl ether myristate is present in an amount of 40 wt %.

28. The method of claim 25, wherein the mixed ester composition is present in an amount of 20 wt %.

29. The method of claim 25, wherein the wax is beeswax.

* * * * *